(12) United States Patent
Hadjiargyrou et al.

(10) Patent No.: US 7,238,799 B2
(45) Date of Patent: Jul. 3, 2007

(54) MUSTANG, A GENE AND NUCLEAR PROTEIN

(75) Inventors: Michael Hadjiargyrou, Coram, NY (US); Frank Lombardo, Lindenhurst, NY (US); David Komatsu, Centerport, NY (US)

(73) Assignee: Research Foundation of State University of New York at Stony Brook, Stony Brook, NY (US)

( * ) Notice: Subject to any disclaimer, the term of this patent is extended or adjusted under 35 U.S.C. 154(b) by 253 days.

(21) Appl. No.: 10/740,052

(22) Filed: Dec. 18, 2003

(65) Prior Publication Data

US 2005/0164206 A1 Jul. 28, 2005

(51) Int. Cl.
*C12P 21/06* (2006.01)
*C12N 5/00* (2006.01)
*C07H 21/04* (2006.01)
*A61K 38/16* (2006.01)

(52) U.S. Cl. .................. 536/23.5; 536/23.1; 536/23.5; 435/69.1; 435/320.1; 435/252.3; 435/325; 530/358

(58) Field of Classification Search ............... 536/23.1, 536/23.5; 435/69.1, 320.1, 252.3, 325; 530/358
See application file for complete search history.

(56) References Cited

U.S. PATENT DOCUMENTS 6,475,735 B1 * 11/2002 Sugiura ........................ 435/6

OTHER PUBLICATIONS

Malek et al. "cDNA clone RGIBG05 from *Rattus norvegicus*," SEQ ID No. 1 alignment result 2, Database: EST, Accession No. BF281834, Nov. 28, 2000.*
Malek et al. "cDNA clone RGIBG05 from *Rattus norvegicus*," SEQ ID No. 2 alignment result 1, Database: EST, Accession No. BF281834, Nov. 28, 2000.*
Jingushi et al., "Genetic expression of extracellular matrix proteins correlates with histologic changes during fracture repair," J bone Miner Res. Sep. 1992;7(9):1045-55.
Hannouche et al., "Current trends in the enhancement of fracture healing.," J Bone Joint Surg Br. Mar. 2001;83(2):157-64.
Sandberg et al., "Gene expression during bone repair," Clin Orthop Relat Res. Apr. 1993;(289):292-312.
Hirakawa et al., "Localization of the mRNA for bone matrix proteins during fracture healing as determined by in situ hybridization," J bone Miner Res. Oct. 1994;9(10):1551-7.
Hiltunen et al., "Expression of type VI, IX and XI collagen genes and alternative splicing of type II collagen transcripts in fracture callus tissue in mice," FEBS Lett. May 8, 1995;364(2):171-4.
Yamazaki et al., "Spatial and temporal expression of fibril-forming minor collagen genes (types V and XI) during fracture healing," J Orthop Res. Sep. 1997;15(5):757-64.
Linkhart et al., "Growth factors for bone growth and repair: IGF, TGF beta and BMP," Bone. Jul. 1996;19(1 Suppl): 1S-12S.
Barnes et al., "Growth factor regulation of fracture repair," J Bone Miner Res. Nov. 1999;14(11):1805-15.
Zhu et al., "Nitric oxide synthase isoforms during fracture healing," Bone Miner Res. Mar. 2001;16(3):535-40.
Sakano et al., "Cartilage-derived retinoic acid-sensitive protein and type II collagen expression during fracture healing are potential targets for Sox9 regulation," J Bone Miner Res. Nov. 1999; 14(11):1891-901.
Uusitalo et al., "Accelerated up-regulation of L-Sox5, Sox6, and Sox 9 by BMP-2 gene transfer during murine fracture healing," J Bone Miner Res. Oct. 2001;16(10):1837-45.
Einhorn et al., "The expression of cytokine activity by fracture callus," J Bone Miner Res. Aug. 1995;10(8):1272-81.
Ohta et al., "Midkine is expressed during repair of bone fracture and promotes chondrogenesis," J Bone Miner Res. Jul. 1999;14(7):1132-44.
Einhorn et al., "The cell and molecular biology of fracture healing," Clin Orthop Relat Res. Oct. 1998(355 Suppl):S7-21.
Matsui et al., "Identification of a dual leucine zipper kinase involved in rat fracture repair," Biochem Biophys Res Commun. Dec. 13, 1996;229(2):571-6.
Diwan et al., "Nitric oxide modulates fracture healing," J Bone Miner Res. Feb. 2000;15(2):342-51.

* cited by examiner

*Primary Examiner*—Jon Weber
*Assistant Examiner*—Rita Mitra
(74) *Attorney, Agent, or Firm*—Medlen & Carroll, LLP

(57) ABSTRACT

The present invention relates to a novel nucleotide sequence and the amino acid sequence encoded therein which comprise a novel gene and protein called Mustang. The present invention also relates to methods and compositions based on these sequences. These sequences are useful in the medical diagnosis, growth and regeneration of bone.

7 Claims, 14 Drawing Sheets

A

```
   1 - GAGCAGCTGTCCCGAGATACGGGATACCCCCTGTCTCCATCTGCTCTCCCCAGGGTGGCTGC -   60
  61 - CCATCATGTCCGAAGAATAAACTCCAGCTAGTCCCTGCCTGATCTGAATCATCTGAGAGC  -  120
 121 - TTCCAAAGAGGGGAGTGACTACCCAGACGACGCACAGGCAGGCTATATAAGTTCCCAAGGG -  180
 181 - CTGGGCTCCACACAGATCTTTGCCTGTCCTGTGCTGGCTACTGCCTGCCAGAGAGTTACCAAAAG -  240
 241 - AGAGCTTGCTTGGCATCTACCATGTCCGAGGCTGGCACTCCTGAAGCTCCCATCAAGAAG  -  300
                M   S   E   A   G   T   P   E   A   P   I   K   K
 301 - AAGCGCCCCCCTGTGAAGGAAGACCTGAAGGGGGCCCGGGGAGTCTGTCCAAGAAC       -  360
        K   R   P   P   V   K   E   E   D   L   K   G   A   R   G   S   L   S   K   N
 361 - CAGGAGATCAAGTCTAAGACGTACCAGGTCATGCGGGACTATGAGCAAGCTGGCTCAGCT   -  420
        Q   E   I   K   S   K   T   Y   Q   V   M   R   D   Y   E   Q   A   G   S   A
 421 - GCCCCATCTATATTCAGCCGCAACCGCACGGGCACCGAGACAGTCTTCGAGAAGCCCAAA  -  480
        A   P   S   I   F   S   R   N   R   T   G   T   E   T   V   F   E   K   P   K
 481 - GAGGGACCTGCCAAGAGCGTCTTTGGCTGTCTTTGGCTGTCTTTGCACTACACCCCCTGGGCA    -  540
        E   G   P   A   K   S   V   F   G   *
 541 - CAGCAACCTGTCCACGAACTCTCTCTCTCTTTTTTTTTTTTAATGCTGGAAGATG       -  600
 601 - CTTTTCCTCTGCCACCTCTGAACCATCTGACTGTCACAACCCTAGCCCTTGGAAACAC    -  660
 661 - CAATAAAGAATAGAGTGCCACTTGGCCCTTCCTGGTCCCGAGGTGGGCTCGGAGAGAGGACA -  720
 721 - GCATATTGAGTGCCCTTCCTGGTCTAGAAAGAGCCTTAGAGACATGGAGTCCTGATACGTGCTTTCA -  780
 781 - GAACCACTGAGGTGTTCTGTCTGTTGCTTTCTCCTAAATCTCTGTTTTAGCCTGGAAAGACGGTGCCAT -  840
 841 - CGGATGTAGAGTAGACTTGCTGTTTCTTTTAGAGGACGCGTGGTTCAATTCCCAAACAGCCGCATG    -  900
 901 - AGCTAAGAGTACTTGCTGTTCTTTTTAGAGGACGCGTGGTTCAATTCCCAAACAGCCGCATG        -  960
 961 - GCTGCTCATAACCATTAACTCTGCCACCCTCTTCTGGCCCTCTGCGGGCATTGCATACAC  - 1020
1021 - GTGGT                                                          - 1025
```

B

```
Rat     1 MSEAGTPEAPIKKKRPPVKEEDLKGARGSLSKNQEIKSKTYQVMRDYEQAGSAAPSIFSRNRTGTETVFEKPKEGPAKSVFG 82
Mouse   1 MSEAGTPBGPIKKKRPPVKEEDLKGARGTLAKNQDIKSSKTYQVMRDYEQAGSAAPSAAPSVFSRNRTGTETVFEKPKEGPAKSVFG 82
Human   1 MSQAGAQEAPIKKKRPPVKEEDLKGARGNLTKNQEIKSKTYQVMRECEQAGSAAPSVFSRTRTGTETVFEKPKAGPTKSVFG 82
Cow     1 MSQAGAQEAPIKKKRPPVKEEDLKGARGNLTKNQEIKSKTYQVMRECEQAGSTAPSVFSRARTGAETVFEKPKAGPAKSVFG 82
```

FIG. 1

A 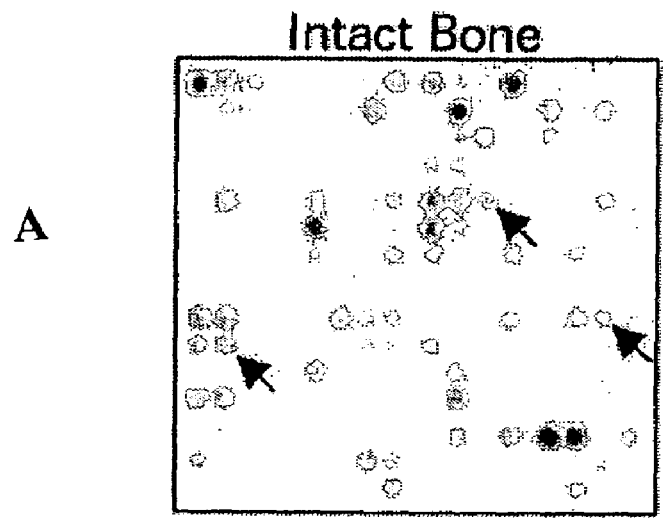
B 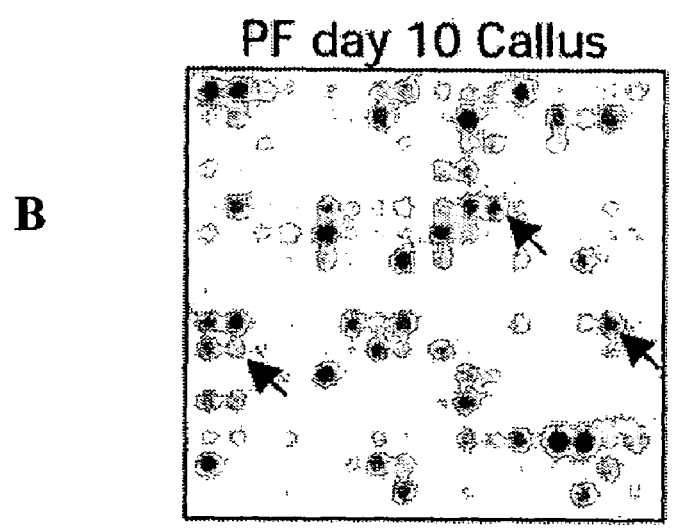
FIG. 3

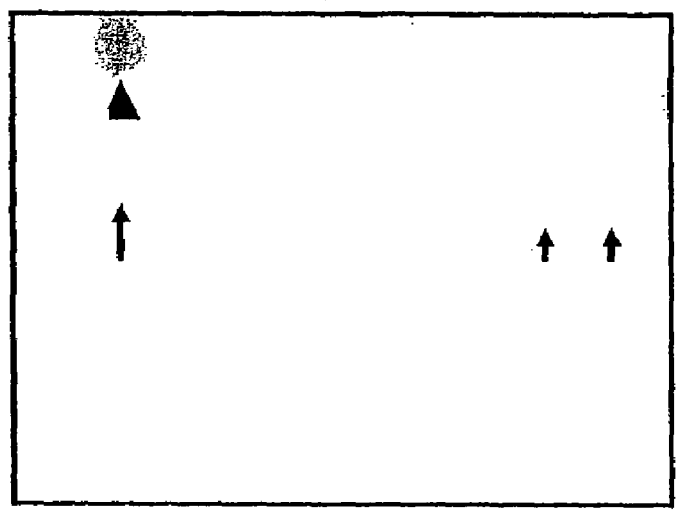
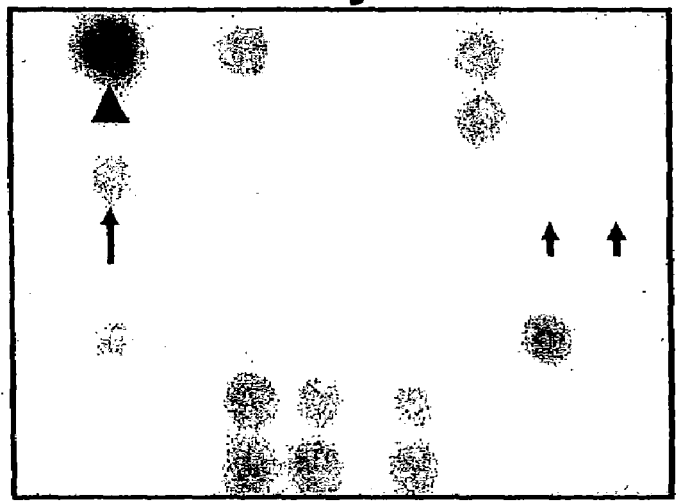
FIG. 7

MUSTANG, A GENE AND NUCLEAR PROTEIN

FIELD OF THE INVENTION

The present invention relates to compositions and methods comprising a novel nucleotide sequence, mustang. This invention also relates to compositions and methods comprising the amino acid sequence encoded therein. Although the present invention is not limited to any particular theory or mechanism, Mustang is localized to the nucleus and is related to skeletal development and regeneration. The present invention also relates to methods for the screening of mustang expression and the use of mustang in gene therapies.

BACKGROUND

Over 6,200,000 fractures of the skeleton occur in the United States each year, with almost 10% complicated by disrupted patterns of bone healing (Einhorn, T. A., *J. Bone Jt. Surg.* 77-A:940–956, 1995). Even with a majority of fractures healing appropriately, over 30,000,000 days each year are lost because of disability or confinement of patients, leading to a tremendous loss of productivity and income. Given the great potential of both tissue and genetic engineering and gene therapy, it is anticipated that exogenous acceleration of fracture healing could increase the overall numbers of fractures that heal successfully, as well as reduce the number of patient days lost due to incapacity.

A number of biochemical and biophysical interventions have been devised with the goal of accelerating the healing of skeletal fractures. The biological strategies include biomimetically inspired skeletal graft substitutes (hydroxyapatite, calcium carbonate), purified or recombinant molecules with chondrogenic and osteogenic attributes (i.e., growth factors), gene therapy and stem cell reservoirs introduced by biodegradable matrices (Hannouche, D., et al., *J. Bone Jt. Surg* 83, 157–164, 2001). The biophysical arsenal includes low intensity ultrasound (Hadjiargyrou, M., et al., *Clin. Orthop* 355, S216–S229, 1998; Rubin, C., et al., *J. Bone Jt. Surg.* 83-A, 259–270, 2001), mechanical stimuli (Kenwright, J. & Gardner, T., *Clin. Orthop.* 355, S179–S190, 1998), and electromagnetic fields (Otter, M. W., et al., *Clin. Orthop.* 355, S90–S104, 1998). While the basic science foundation supporting these modalities is strong, the clinical results have been inconclusive. Therefore, it becomes reasonable to conclude that the complexity of the healing process is being underestimated and that the healing process cannot ultimately be determined by a singular idealized molecule, material, or stimulus.

The great majority of studies that have examined the molecular basis of healing have focused on the expression of specific genes, with the bulk of these studies concentrating on the regulatory role of known extracellular matrix (ECM)1 genes (Jingushi, S., et al., *J. Bone Miner. Res.* 7:1045–1055, 1992; Sandberg, M. M., et al., *Clin. Orthop. Rel. Res.* 289:292–312, 1993; Hirakawa, K., et al., *J. Bone Miner. Res.* 9:1551–1557, 1994; Hiltunen, A., et al., *FEBS Lett.* 364: 171–174, 1995; Yamazaki, M., et al., *J. Orthop. Res.* 15:757–764, 1997) and growth factor genes and proteins (Linkhart, T. A., et al., *Bone* (NY) 19, 1S–19S, 1996; Barnes, G. L., et al., *J. Bone Miner. Res.* 14:1805–1815, 1999). The range of genes evaluated has recently expanded to include other protein families, including intracellular signaling molecules (Zhu, W., et al., *J. Bone Miner. Res.* 16:535–540, 2001), transcription factors (Sakano, S., et al., *J. Bone Miner. Res.* 14:1891–1901, 1999; Uusitalo, H., et al., *J. Bone Miner. Res.* 16:1837–1845, 2001), cytokines (Einhorn, T. A., et al., *J. Bone Miner. Res.* 10:1272–1281, 1995; Ohta, S., et al., *J. Bone Miner. Res.* 14:1132–1144, 1999), adhesion molecules (Einhorn, T. A., *Clin. Orthop.* 355, S7–21, 1998), and enzymes (Matsui, N., et al., *Biochem. Biophys. Res. Commun.* 229:571–576, 1996; Diwan, A. D., et al., *J. Bone Miner. Res.* 15:342–351, 2000). While this body of work has helped demonstrate the temporal and spatial roles of specific genes, it has also served to indicate that we have limited knowledge of how extensive the transcriptional control of the repair process may be or identify specific genes and processes that are the critical regulators of successful bone healing.

Given the biological complexity of fracture healing, a process morphologically characterized by inflammation, chondrogenesis, and osteogenesis, it is reasonable to hypothesize that it is regulated by a very large number of transcriptional events (Hadjiargyrou, M., et al., *J. Bone Miner. Res.* 15:1014–1023, 2000; Hadjiargyrou, M., et al., *Bone* (NY) 9:149–154, 2000). This hypothesis is supported by the marked similarities between the repair process of bone and embryonic development of the skeleton, marked by key cellular events (migration, adhesion, proliferation, and differentiation), all of which require the tightly orchestrated activity of thousands of proteins whose expression patterns rely on both extracellular and intracellular signals. However, little is known in the prior art about the actual processes or the genes involved.

What is need are novel compositions and methods for use in the diagnosis, screening and therapeutic intervention (e.g., gene therapies) in relation to bone healing and regeneration.

SUMMARY OF THE INVENTION

The present invention generally relates to compositions and methods used in the medical diagnosis, growth and regeneration (i.e., healing) of bone. It is not intended that the present invention be limited to particular method of diagnosis and treatment. Additionally, in another embodiment, the present invention relates to the compositions and methods used in scientific investigation.

The nuclotide and amino acid sequences of the present invention have been identified as a gene and gene product that are activated during bone generation and repair. although the present invention is not limited to any particular mechanism and an understanding of the mechanism is not required to practice the present invention, it is believed that mustang encodes a nuclear protein that is instrumental in the control and/or regulation of bone growth and regeneration, or instrumental in the processes required for the growth and regeneration of bone. In one embodiment, it is contemplated that the sequences of the present invention are used for the diagnosis, treatment and prevention of bone diseases and bone repair diseases (e.g., osteoporosis, myeloma bone disease and bone growth disorders such as osteopetrotic diseases, e.g., Paget's disease, Albers-Schonberg Disease, Generalized Congenital Osteosclerosis, Ivory Bones, Marble Bones and Osteosclerosis Fragilis Generalisata). In another embodiment, it is contemplated that the sequences of the present invention are used for to promote the growth and healing of bone through, for example, gene therapy techniques.

In one embodiment, the present invention contemplates an isolated nucleic acid encoding at least a fragment of the mustang gene (SEQ ID NO: 1) or protein (SEQ ID NO: 2) set forth in FIG. 1, including native and mutant sequences (e.g., SEQ ID NOS: 1 and 2 comprising one or more nucleotide base or amino acid changes, respectively).

It is not intended that the present invention be limited as to the specific nature of the nucleic acid encoding the peptides described above, (i.e. the "transgene") or portions thereof. In one embodiment, said nucleic acid is contained in a vector. In another embodiment, said vector is in a host cell. In yet another embodiment, said vector is in a transgenic animal. Additionally, said gene may integrate into the genome of the transgenic animal. In a particular embodiment, the transgenic animal of the present invention may be generated with the transgene contained in an inducible, tissue specific promoter.

In one embodiment, the present invention also contemplates RNA transcribed from the above-indicated cDNA as well as protein (typically purified protein) translated from this RNA. Moreover, the present invention contemplates antibodies produced from immunizing with this translated protein or antigen epitopes thereof.

In one embodiment, the present invention contemplates using the above-named compositions in screening assays. The present invention is not limited by the particular method of screening. In one embodiment, cells are used such as, but not limited to, transformed cell lines. In another embodiment, primary cells may be used. The present invention is not limited to the nature of the transfection construct. The transfection constructs utilized are the optimal constructs available for the cell line chosen at the time of setting up the assay. In one embodiment, the present invention contemplates screening suspected compounds (e.g., drug candidates) in a system utilizing transfected cell lines. In one embodiment, the cells are transfected transiently. In another embodiment, the cells are stably transfected. In yet another embodiment translation products of the invention are used in a cell-free assay system. In yet another embodiment, antibodies generated to the translation products of the invention are used in immunoprecipitation assays or used in vivo.

Furthermore, the present invention is also used to identify Mustang binding partners and interactive proteins. In one embodiment, antibodies generated to translation products of the invention are used in immunoprecipitation experiments to isolate peptides that interact with Mustang. In another embodiment, the invention is used to generate fusion proteins that are used to isolate interactive proteins. In yet another embodiment, screens are conducted using the yeast two-hybrid system.

In another embodiment, peptides of the invention is used in microchip assays. For example, the present invention contemplates a method of screening, comprising: a) providing in any order: i) a first solid support (e.g. microchip) comprising peptides or peptide fragments from a library of the species to be examined and ii) a peptide, or portion thereof, encoded by the DNA of SEQ ID NO:1; b) contacting said microassay microchips with said peptide under conditions such that binding occurs.

In one embodiment, the present invention is also used to identify new homologs of Mustang or natural mutations thereof. The present invention contemplates screening for homologs using standard molecular procedures. In another embodiment, screens are conducted using Northern and Southern blotting.

In one embodiment, the present invention contemplates a method of screening a compound, said method comprising: a) providing in any order: i) a first group of cells comprising a recombinant expression vector, wherein said vector comprises at least a portion of the oligonucleotide sequence of SEQ ID NO:1, ii) and a test compound; b) contacting said first and second groups of cells with said compound; and c) detecting the effects of said compound. In still another embodiment, a second group of cells comprise a recombinant expression vector, wherein said vector comprises a suitable control (e.g., an empty vector).

In one embodiment, the present invention also contemplates a method of screening for homologs, said method comprising: a) providing in any order: i) a nucleic acid comprising at least a portion of the sequence of SEQ ID NO: 1, and ii) DNA libraries from cells or tissues suspected to comprise said homolog; and b) hybridizing said first or second nucleic acid with said DNA of said library under conditions such that said DNA suspected of coding for said homolog is detected.

In one embodiment, the present invention also contemplates a method of screening for interactive peptides, said method comprising: a) providing in any order: i) a peptide comprising at least a portion of the peptide sequence of SEQ ID NO: 2 (including but not limited to portions that are part of fusion proteins, e.g., proteins that contain another portion, such as a portion useful for protein purification) and b) an extract from source (e.g., cells or tissues) suspected of having said interactive peptides; and c) mixing said peptide with said extract under conditions such that said interactive peptide is detected.

In one embodiment, the present invention also contemplates an approach for screening for interactive peptides, said method comprising: a) providing in any order: i) antibodies reactive with (e.g., specific for) at least a portion of a peptide having the sequence of SEQ ID NO: 2, and ii) an extract from a source (e.g., cells or tissues) suspected of having said interactive peptide(s); and b) mixing said antibody with said extract under conditions such that said interactive peptide is detected.

In one embodiment, the present invention contemplates the generation of cell lines that express the mustang gene, or portion thereof. The present invention is not limited to any particular cell line (e.g., osteoblasts, osteocytes, osteoclasts or chondrocytes, etc., as well as the peritoneal lining of the bones).

In one embodiment, the present invention contemplates DNA binding assays where a) mustang DNA (e.g., SEQ ID NO:1), or portion thereof, is either i) adhered to a solid support surface or ii) placed in a suspension, b) compounds suspected of binding to the DNA are added in a manner that promotes binding and c) binding is measured. Detection methods utilized include, but are not limited to, staining, gel electrophoresis and spectrophometric methods.

In one embodiment, the present invention contemplates high throughput screening methods. Such methods include, but are not limited to, DNA array assays, spectrophotometric assays, mass spectometry, the use of robotics, the use of computerized assay systems and the use of commercially available systems.

In one embodiment, the present invention contemplates screening for proteins that bind to mustang gene binding sites. The present invention is not limited to any particular assay method. In one embodiment, DNA encoding the sequences of the present invention (proteins encoded by SEQ ID NO: 1 or portions thereof) is attached to a solid surface (e.g., a microchip) and protein suspected of binding the DNA sequences is placed in contact with the DNA. Attached proteins are then analyzed by methods know to those in the art.

In one embodiment, the present invention contemplates prenatal testing for mutant mustang genes. Such techniques are known in the art. For example, parents or fetuses can be screened for mutant mustang alleles.

In one embodiment, the present invention contemplates a method, comprising: a) providing in any order: i) a first solid support comprising nucleic acid from a DNA library of the species to be examined and ii) an oligonucleotide, selected form a group consisting of SEQ ID NO: 1 and portions thereof; b) contacting said solid support with said oligonucleotide under conditions such that hybridization takes place. In one embodiment, the present invention contemplates the solid support is a microchip.

In one embodiment, the present invention contemplates a method of screening a compound, said method comprising: a) providing in any order: i) a first group of cells comprising a recombinant expression vector, wherein said vector comprises at least a portion of the an oligonucleotide, selected form a group consisting of SEQ ID NO:1 and portions thereof, ii) a second group of cells comprising a recombinant expression vector, wherein said vector comprises an empty vector, and iii) a test compound; b) contacting said first and second groups of cells with said compound to produce mustang expression; and c) culturing said cells under conditions such that said mustang expression is detected.

In one embodiment, the present invention contemplates a method of screening for homologs, said method comprising: a) providing in any order: i) a nucleic acid comprising at least a portion of an oligonucleotide, selected form a group consisting of SEQ ID NO: 1 and portions thereof, and ii) DNA libraries from cells or tissues suspected to comprise said homolog; and b) hybridizing said first or second nucleic acid with said DNA of said library under conditions such that said DNA suspected of coding for said homolog is detected.

In one embodiment, the present invention contemplates a method comprising: a) providing in any order: i) a peptide comprising at least a portion of the peptide sequence of SEQ ID NO: 2 and ii) an extract from source suspected of having one or more interactive peptides; and c) mixing said peptide with said extract under conditions such that said one or more interactive peptides is detected. In one embodiment, the peptide is a fusion protein.

In one embodiment, the present invention contemplates a method comprising: a) providing in any order: i) antibodies reactive with at least a portion of a peptide having the sequence of SEQ ID NO: 2, and ii) an extract from a source suspected of having one or more interactive peptides; and b) mixing said antibody with said extract under conditions such that said one or more interactive peptides is detected. In one embodiment, the peptide is a fusion protein.

In one embodiment, the present invention contemplates a method of identifying subjects who have mutant mustang genes, comprising: a) providing nucleic acid from a subject, wherein the nucleic acid is selected from a group comprising mustang genes or portions thereof, and b) detecting the presence or absence of one or more variations in the gene. In another embodiment, the present invention contemplates that the variation is a single nucleotide polymorphism. In yet another embodiment, the present invention contemplates that the variation causes a frameshift mutation in mustang. In yet another embodiment, the present invention contemplates that the variation causes a splice mutation in mustang. In yet another embodiment, the present invention contemplates that the variation causes a nonconservative amino acid substitution, insertion and deletion in mustang. In yet another embodiment, the present invention contemplates that the detecting in step b) is accomplished by hybridization analysis. In yet another embodiment, the present invention contemplates that the detecting in step b) comprises comparing the sequence of the nucleic acid to the sequence of a wild-type mustang nucleic acid.

In one embodiment, the present invention contemplates an isolated nucleic acid comprising a sequence encoding a polypeptide selected from the group consisting of SEQ ID NO: 2 and portions thereof. In another embodiment, the present invention contemplates that the nucleic acid sequence is operably linked to a heterologous promoter. In yet another embodiment, the present invention contemplates that a nucleic acid sequence, wherein the sequence is contained within a vector. In yet another embodiment, the present invention contemplates a host cell comprising the vector of the previous embodiment. In yet another embodiment, the present invention contemplates the host cell of the previous embodiment, wherein the host cell is selected from the group consisting of animal and plant cells. In yet another embodiment, the present invention contemplates a host cell of the previous embodiment, wherein the host cell is located in an organism.

In one embodiment, the present invention contemplates an isolated nucleic acid sequence comprising the sequence of SEQ ID NO: 1. In another embodiment, the present invention contemplates a computer readable medium encoding a representation of SEQ ID NO: 1.

In one embodiment, the present invention contemplates an isolated polypeptide comprising the amino acid sequence of SEQ ID NO: 2. In another embodiment, the present invention contemplates a computer readable medium encoding a representation of the polypeptide of SEQ ID NO: 2.

In one embodiment, the present invention contemplates a method of treating a patient with abnormal bone growth, regeneration or repair, comprising administering a therapeutically effective amount of an Mustang (e.g., SEQ ID NO: 2 or portion thereof) such that the symptoms of the disease are alleviated, wherein the mustang is selected from the group consisting of: recombinant Mustang; synthetic Mustang; mutants, variants, fragments, and fusions of recombinant Mustang; and mutants, variants, fragments, and fusions of synthetic Mustang.

In one embodiment, the present invention relates to the delivery of exogenous nucleic acids to cells (e.g., SEQ ID NO: 1), including but not limited to the cells of multicellular organisms. When the nucleic acid includes an expressible gene, that gene can be expressed in the cell. In some embodiments, a tissue-specific carrier molecule is prepared, which is a bifunctional molecule having a nucleic acid-binding moiety and a target tissue-binding moiety.

In one embodiment, the nucleic acid can be compacted at high concentrations with the carrier molecule at a critical salt concentration. The nucleic acid-loaded carrier molecule is then administered to the organism.

In one embodiment, the present invention is not limited to any particular method for the delivery of the oligonucleotide to the organism. Many different methods are contemplated. For example, in one embodiment, the present invention contemplates a method for delivering an oligonucleotide to a mammalian cell, comprising the steps of: a) providing: i) a target binding moiety capable of binding to a serpin enzyme (or osteopontin or CD44, for example) complex receptor; ii) a nucleic acid binding moiety; iii) an expression vector comprising an oligonucleotide encoding one or more gene products; iv) a mammalian cell having on its exterior surface a serpin enzyme complex receptor; b) conjugating the target binding moiety to the nucleic acid binding moiety to form a carrier; c) coupling the expression vector with the carrier to form a pharmaceutical composition; and d) contacting the mammalian cell with the pharmaceutical composition under conditions such that the pharmaceutical composition binds to the receptor and results in delivery of the pharmaceutical composition to the interior of the mammalian cell. It is preferred that the expression vector (i.e., the nucleic acid or oligonucleotide encoding one or more gene products) is compacted. The compaction of nucleic acids (e.g., expression vectors) associated with a carrier comprising a conjugate between a TBM and a NABM is described in detail herein. Preferably, the pharmaceutical compound comprising the carrier and the expression vector are compacted to a diameter of less than 100 nm, preferably less than 80 nm and most preferably having a diameter of about 10 to 25 nm, with a diameter of about 15 to 25 nm being particularly preferred. Additionally, in another embodiment, the methods of Ferkol, et al., (U.S. Pat. Nos. 5,972,900; 5,972,901 and 6,200,801) are contemplated as methods of the present invention and are incorporated herein by reference.

In a preferred embodiment, the expression vector further comprises a promoter sequence operably linked to the oligonucleotide encoding one or more gene products. The present invention is not limited by the nature of the promoter sequence employed. Any promoter sequence which is functional in the target cell (e.g., osteoblasts and chondrocytes and cells of the periosteum of the bone) may be employed to achieve expression of the gene(s) of interest. The promoter sequence may be from a mammalian gene, including but not limited to the gene encoded by the expression vector (i.e., the gene(s) of interest present on the expression vector may be under the transcriptional control of their native or endogenous promoter).

In one embodiment, the promoter sequence may be derived (i.e., obtained or isolated) from a gene expressed in all mammalian cells (i.e., a constitutive or ubiquitous promoter) such as β-actin, human elongation factor 1α gene, etc. Alternatively, the promoter may be derived from a gene which is expressed in a tissue-specific manner so long as the promoter is active in the target cell. For example, when bone cells are the target cells, promoters derived from genes expressed in bone such as, for example, the osteopontin promoter may be employed.

Alternatively, in another embodiment, the promoter may be derived from viral sequences, such as viral long terminal repeats (LTRs), which are expressed in a variety of cell types. For example, the LTR of the Rous sarcoma virus (RSV), Moloney murine leukemia virus (MoMLV) and the human cytomegalovirus (CMV) may be used in the present invention. However, it is not intended that the viral promoter be limited to a particular viral promoter as various promoters may be used in the present invention.

In one embodiment, the expression vector may also comprise an enhancer sequence. Transcriptional control signals in eucaryotes comprise "promoter" and "enhancer" elements or sequences. Promoters and enhancers consist of short arrays of DNA sequences that interact specifically with cellular proteins involved in transcription [Maniatis, et al., *Science* 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types [for review see Voss, et al., *Trends Biochem. Sci.*, 11:287 (1986) and Maniatis, et al., supra (1987)]. For example, the SV40 early gene enhancer is very active in a wide variety of cell types from many mammalian species and has been widely used for the expression of proteins in mammalian cells [Dijkema, et al., *EMBO J.* 4:761 (1985)]. Two other examples of promoter/enhancer elements active in a broad range of mammalian cell types are those from the human elongation factor 1α gene [Uetsuki et al., *J. Biol. Chem.*, 264:5791 (1989); Kim et al., *Gene* 91:217 (1990); and Mizushima and Nagata, *Nuc. Acids. Res.*, 18:5322 (1990)], the LTRs of the Rous sarcoma virus [Gorman et al., *Proc. Natl. Acad. Sci. USA* 79:6777 (1982)], and the human cytomegalovirus [Boshart et al., *Cell* 41:521 (1985)].

In one embodiment, the enhancer and/or promoter sequences employed may be "endogenous" or "exogenous" or "heterologous." An endogenous enhancer or promoter is one which is naturally linked with a given gene in the genome. An exogenous (heterologous) enhancer or promoter is one which is placed in juxtaposition to a gene by means of genetic manipulation (i.e., molecular biological techniques known to those in the art).

It is not intended that the present invention be limited by the nature of the nucleic acid binding moiety. In one embodiment, the nucleic acid binding moiety is a polycation, such as poly-L-lysine. Other nucleic acid binding moieties including, but not limited to protamines, polyarginine, avidin (employed when the expression vector comprises biotin moieties), polyornithine, and histones may be employed.

The term "polycation" as used herein refers to a peptide or polypeptide (i.e., protein) sequence which contains an abundance of amino acid residues having positively charged (i.e., basic) side chains (e.g., arginine and lysine) such that the peptide has a positive charge and is capable of binding ionically to nucleic acids (which are negatively charged). Preferably the polycation comprises at least 4 amino acid residues.

In one embodiment, the present invention is not limited by the location of the recipient or target cell. The target cell may be a cultured cell or more preferably the cell may be located in a recipient animal, including a human. In a preferred embodiment, the recipient mammalian cell is selected from the group consisting of osteoblasts, osteocytes, osteoclasts, chondrocytes, etc.

In a preferred embodiment, the contacting of the mammalian cell with the pharmaceutical (i.e., therapeutic) composition comprises administrating the complex to the recipient animal. The present invention is not limited by the nature of the administration of the composition. In one embodiment, the administration comprises injection of an aqueous solution containing the pharmaceutical composition into the recipient animal (e.g., by intravenous injection).

In one embodiment, the present invention can be used with success with a variety of animals. Particular therapeutic success is achieved with humans. In that regard, it may be desirable, following injection of the composition, to examine the relevant tissue for the expression of the one or more gene products encoded by the expression vector.

In a preferred embodiment, the method of the present invention further comprises, following contacting the mammalian cell with the pharmaceutical composition, examining the contacted cell for the expression of the one or more gene products encoded by the expression vector.

It is not intended that the present invention be limited by the nature of the nucleic acid binding moiety. In one embodiment, the nucleic acid binding moiety is a polycation, such as poly-L-lysine. Other nucleic acid binding moieties such as protamines, polyarginine, avidin (employed when the expression vector comprises biotin moieties), polyornithine and histones may be employed.

The present invention is not limited by the nature of the nucleic acid binding moiety present on the fusion protein. In a preferred embodiment, the nucleic acid binding moiety comprises at least a portion of a protamine protein. The invention is not limited by the source of the protamine; protamine isolated from a variety of sources (e.g., rat, mouse, human, fish, etc.) is contemplated.

In one embodiment, the fusion proteins of the present invention may be produced using a variety of approaches known to the art, including but not limited to chemical synthesis of the desired peptide sequence or expression of the desired fusion protein by molecular biological means (i.e, construction of an expression vector containing a coding region encoding the desired fusion protein).

In one embodiment, the present invention contemplates an isolated nucleic acid sequence comprising SEQ ID NO: 1. In another embodiment, the present invention contemplates that the nucleic acid sequence is operably linked to a heterologous promoter. In still another embodiment, the present invention contemplates the nucleic acid sequence linked to the heterologous promoter is contained within a vector. In still yet another embodiment, the present invention contemplates that said vector is in a host cell. In still yet another embodiment, the present invention contemplates that the host cell is selected from the group consisting of osteoblasts, osteocytes, osteoclasts and chondrocytes. In still yet another embodiment, the present invention contemplates that the vector comprising the nucleic acid sequence was transfected into the host cell under conditions wherein the protein encoded by SEQ ID NO:1 is expressed.

In one embodiment, the present invention contemplates an isolated nucleic acid comprising a sequence encoding the polypeptide of SEQ ID NO: 2. In another embodiment, the present invention contemplates that the nucleic acid sequence is operably linked to a heterologous promoter. In yet another embodiment, the present invention contemplates that the nucleic acid sequence is contained within a vector. In still yet another embodiment, the present invention contemplates that the vector is in a host cell. In still yet another embodiment, the present invention contemplates that the host cell is selected from the group consisting of osteoblasts, osteocytes, osteoclasts and chondrocytes. In still yet another embodiment, the present invention contemplates that the host cell was transfected with said vector under conditions wherein the protein having the amino acid sequence set forth in SEQ ID NO:2 is expressed.

In one embodiment, the present invention contemplates an isolated polypeptide comprising the amino acid sequence of SEQ ID NO: 2.

In one embodiment, the present invention contemplates a method, comprising: a) providing: i) a patient with symptoms of a condition selected from the group consisting of abnormal bone growth, abnormal bone regeneration and abnormal bone repair; and ii) an assay for measuring the level of expression of a protein having the amino acid sequence set forth in SEQ ID NO: 2; b) obtaining cells from said patient; and c) measuring the level of expression of said protein with said assay. In another embodiment, the present invention contemplates the above method, wherein said symptoms are selected from the group consisting of diminished bone density, increased bone density, abnormal decrease in bone size, abnormal increase in bone size, reduced joint mobility, abnormal bone fusion, easily broken bones and poor bone fracture healing. In yet another embodiment, the present invention contemplates the above method, wherein said cells are obtained by biopsy. In still yet another embodiment, the present invention contemplates the above method, wherein said cells are selected from the group consisting of osteoblasts, osteocytes, osteoclasts and chondrocytes.

In one embodiment, the present invention contemplates a method, comprising: a) providing: i) a patient with symptoms of a condition selected from the group consisting of abnormal bone growth, abnormal bone regeneration and abnormal bone repair; and ii) an assay for detecting variations in the nucleic acid sequence set forth in SEQ ID NO:1; b) obtaining cells from said patient, said cells comprising nucleic acid; and c) assaying said nucleic acid with said assay under conditions such that at least one variation in the SEQ ID NO: 1 is detected. In another embodiment, the present invention contemplates the above method, wherein said symptoms are selected from the group consisting of diminished bone density, increased bone density, abnormal decrease in bone size, abnormal increase in bone size, reduced joint mobility, abnormal bone fusion, easily broken bones and poor bone fracture healing. In yet another embodiment, the present invention contemplates the above method, wherein said cells are obtained by biopsy. In still yet another embodiment, the present invention contemplates the above method, wherein said cells are selected from the group consisting of osteoblasts, osteocytes, osteoclasts and chondrocytes. In still yet another embodiment, the present invention contemplates the above method, wherein said variation comprises a single nucleotide polymorphism. In still yet another embodiment, the present invention contemplates the above method, wherein said variation comprises a frameshift mutation. In still yet another embodiment, the present invention contemplates the above method, wherein said variation comprises a splice mutation. In still yet another embodiment, the present invention contemplates the above method, wherein said variation comprises a mutation which causes a nonconservative amino acid substitution. In still yet another embodiment, the present invention contemplates the above method, wherein said assay comprises hybridization analysis.

In one embodiment, the present invention contemplates a method of detecting a subject at risk for a condition selected from the group consisting of abnormal bone growth, abnormal bone regeneration and abnormal repair, comprising: a) providing a bone biopsy sample from a subject, wherein the bone biopsy sample comprises polypeptides; and, b) detecting at least one variant of SEQ ID NO: 2 in said polypeptides. In another embodiment, the present invention contemplates the above method, wherein said detecting of step b) is accomplished by an antibody assay.

In one embodiment, the present invention contemplates a method of detecting a subject at risk for a condition selected from the group consisting of abnormal bone growth, abnormal bone regeneration and abnormal repair, comprising: a) providing a sample comprising nucleic acid from a subject, wherein the bone biopsy sample comprises nucleic acid; and, b) detecting at least one variant of SEQ ID NO: 1 in said nucleic acid. In another embodiment, the present invention contemplates the above method, wherein said detecting of step b) is accomplished by a hybridization assay.

In one embodiment, the present invention contemplates a method of treatment, comprising: a) providing: i) a patient with symptoms of a condition selected from the group consisting of abnormal bone growth, abnormal bone regeneration and abnormal bone repair; and ii) a composition comprising a protein having the sequence set forth in SEQ ID NO: 2; and b) administering a therapeutically effective amount of said composition under conditions such that at least one symptom is reduced. In another embodiment, the present invention contemplates the above method, wherein said symptoms are selected from the group consisting of diminished bone density, increased bone density, abnormal decrease in bone size, abnormal increase in bone size, reduced joint mobility, abnormal bone fusion, easily broken bones and poor bone fracture healing.

In one embodiment, the present invention contemplates a method of detecting a subject at risk for a condition selected from the group consisting of abnormal bone growth, abnormal bone regeneration and abnormal repair, comprising: a) providing a bone biopsy sample from a subject, wherein the bone biopsy sample comprises polypeptides; and, b) measuring the level of expression of SEQ ID NO: 2 in said polypeptides. In another embodiment, the present invention contemplates the above method, wherein said symptoms are selected from the group consisting of diminished bone density, increased bone density, abnormal decrease in bone size, abnormal increase in bone size, reduced joint mobility, abnormal bone fusion, easily broken bones and poor bone fracture healing.

In one embodiment, the present invention contemplates a method for transfecting a mammalian cell, comprising the steps of: a) providing: i) a target binding moiety capable of binding to a receptor selected form a group consisting of CD44 and osteopontin; ii) a nucleic acid binding moiety; iii) an expression vector comprising the nucleotide sequence set forth in SEQ ID NO: 1; and iv) a mammalian cell having on its exterior surface a receptor selected from the group consisting of CD44 and osteopontin; b) conjugating said target binding moiety to said nucleic acid binding moiety to form a carrier; c) coupling said expression vector with said carrier to form a pharmaceutical composition; and d) contacting said mammalian cell with said pharmaceutical composition under conditions such that said mammalian cell is transfected. In another embodiment, the present invention contemplates the above method, wherein said expression vector further comprises a promoter sequence operably linked to said nucleic acid sequence set forth in SEQ ID NO:1. In yet another embodiment, the present invention contemplates the above method, wherein said promoter sequence is a viral promoter sequence. In still yet another embodiment, the present invention contemplates the above method, wherein said expression vector is compacted. In still yet another embodiment, the present invention contemplates the above method, wherein said mammalian cell is located in a recipient animal. In still yet another embodiment, the present invention contemplates the above method, wherein said mammalian cell is selected from the group consisting of osteoblasts, osteocytes, osteoclasts and chondrocytes.

In one embodiment, the present invention contemplates a method of detecting proteins interactive with at least a portion of SEQ IN NO:1, comprising: a) providing: i) a nucleic acid coding for at least a portion of SEQ ID NO: 1; ii) a yeast two-hybrid detection system; b) introducing said nucleic acid into said yeast two-hybrid detection system; c) detecting one or more proteins that interact with the expression products of said nucleic acid.

Definitions

As used herein, a "pharmaceutical composition" is a composition comprising an aggregate (i.e., a complex) between an expression vector (i.e., a nucleic acid molecule) and a carrier comprising a target binding moiety conjugated to a nucleic acid binding moiety. The pharmaceutical composition may further comprise a pharmaceutically acceptable excipient. The terms "pharmaceutical composition" and therapeutic composition" are used herein interchangeably. It is not intended that the pharmaceutical compositions be limited to any particular expression vector, carrier or exciepient.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

In particular, the terms "Mustang," "Mustang peptide" and "Mustang protein" refer to a full-length Mustang amino acid sequence (e.g., as shown in SEQ ID NO:2). However, it is also intended that the term encompass fragments of SEQ ID NO: 2, as well as other domains with the full-length amino acid sequence. Furthermore, the terms "Mustang amino acid sequence" or "Mustang polypeptide" encompass SEQ ID NO: 2.

The term "portion" when used in reference to a protein (as in "a portion of a given protein") refers to fragments of that protein. The fragments may range in size from four amino acid residues to the entire amino sequence minus one amino acid. The term"potion" when used in reference to a nucleic acid (as in "a portion of a given nucleic acid") refers to fragments of that nucleic acid. The fragments may range in size from ten bases to the entire nucleic acid sequence minus one base.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences includes those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80% sequence identity, preferably at least 90% sequence identity, more preferably at least 95% sequence identity or more (e.g., 99% sequence identity). Preferably, residue positions which are not identical differ by conservative amino acid substitutions.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, preferably less than 5% and still more preferably less than 2% changes (whether substitutions, deletions, and so on).

The term "domain" when used in reference to a polypeptide refers to a subsection of the polypeptide which possesses a unique structural and/or functional characteristic; typically, this characteristic is similar across diverse polypeptides. The subsection typically comprises contiguous amino acids, although it may also comprise amino acids which act in concert or which are in close proximity due to folding or other configurations.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene. SEQ ID NO: 1 of the present invention comprises the mustang gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

In particular, the term "mustang gene" refers to a full-length mustang nucleotide sequence (e.g., as shown in SEQ ID NO:1). However, it is also intended that the term encompass fragments of the SEQ ID NO: 1, as well as other domains with the full-length nucleotide sequence. Furthermore, the terms "mustang nucleotide sequence" or "mustang polynucleotide sequence" encompass DNA, cDNA, and RNA (e.g., mRNA) sequences.

The term "heterologous" when used in reference to a gene refers to a gene encoding a factor that is not in its natural environment (i.e., has been altered by the hand of man). For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise, e.g., plant or animal gene sequences that comprise cDNA forms of a plant or animal gene; the cDNA sequences may be expressed in either a sense (to produce mRNA) or anti-sense orientation (to produce an anti-sense RNA transcript that is complementary to the mRNA transcript). Heterologous genes are distinguished from endogenous genes in that the heterologous gene sequences are typically joined to nucleotide sequences comprising regulatory elements such as promoters that are not found naturally associated with the gene for the protein encoded by the heterologous gene or with gene sequences in the chromosome, or are associated with portions of the chromosome not found in nature (e.g., genes expressed in loci where the gene is not normally expressed). In the present invention, it is contemplated that SEQ ID NO: 1 and portions thereof may comprise a heterologous gene. For example, SEQ ID NO:1 may be joined to promoter specific for connective tissues of skeletal tissues. Examples of such promoters include, but are not limited to the osteopontin promoter, the bone morphogenetic protein-2 (BMP-2) promoter, the fibronectin promoter and the chondronectin promoter.

The term "nucleotide sequence of interest" or "nucleic acid sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The terms "oligonucleotide" or "polynucleotide" or "nucleotide" or "nucleic acid" refer to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The terms "an oligonucleotide having a nucleotide sequence encoding a gene" or "a nucleic acid sequence encoding" a specified polypeptide refer to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The following terms are used to describe the sequence relationships between two or more polynucleotides: "reference sequence," "sequence identity," "percentage of sequence identity" and "substantial identity." A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20% or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Nati. Acad. Sci.*

(U.S.A.) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95% sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4(H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4(H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4(H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is frequently that gene which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product. In the present invention, SEQ ID NO: 1 comprises the wild-type gene.

Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

The term "polymorphic locus" refers to a genetic locus present in a population that shows variation between members of the population (i.e., the most common allele has a frequency of less than 0.95). Thus, "polymorphism" refers to the existence of a character in two or more variant forms in a population. A "single nucleotide polymorphism" (or SNP) refers a genetic locus of a single base which may be occupied by one of at least two different nucleotides. In contrast, a "monomorphic locus" refers to a genetic locus at which little or no variations are seen between members of the population (generally taken to be a locus at which the most common allele exceeds a frequency of 0.95 in the gene pool of the population).

A "frameshift mutation" refers to a mutation in a nucleotide sequence, usually resulting from insertion or deletion of a single nucleotide (or two or four nucleotides) which results in a change in the correct reading frame of a structural DNA sequence encoding a protein. The altered reading frame usually results in the translated amino-acid sequence being changed or truncated.

A "splice mutation" refers to any mutation that affects gene expression by affecting correct RNA splicing. Splicing mutation may be due to mutations at intron-exon boundaries which alter splice sites.

The term "detection assay" refers to an assay for detecting the presence or absence of a sequence or a variant nucleic acid sequence (e.g., mutation or polymorphism in a given allele of a particular gene, as e.g., mustang gene [SEQ ID NO: 1]), or for detecting the presence or absence of a particular protein (e.g., mustang [SEQ ID NO: 2]) or the structure or activity or effect of a particular protein (e.g., a binding assay or activity assay) or for detecting the presence or absence of a variant of a particular protein.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlain et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and into protein, through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination," "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987). In the present invention, it is contemplated that, for example, SEQ ID NO: 1 may be joined to promoter specific for connective tissues of skeletal tissues. Examples of such promoters include, but are not limited to the osteopontin promoter, the bone morphogenetic protein-2 (BMP-2) promoter, the fibronectin promoter and the chondronectin promoter. Additionally, it is contemplated that SEQ ID NO: 1 may be joined to a constitutive promoter or an inducible promoter (both defined below) or to a promoter specific for other cell or tissue types (defined below) (e.g., promoters specific for muscle or skin).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length.

Promoters may be tissue specific or cell specific. Examples of promoters specific for bone and connective tissues are given above. The term "tissue specific" as it applies to a promoter refers to a promoter that is capable of directing selective expression of a nucleotide sequence of interest to a specific type of tissue (e.g., muscle) in the relative absence of expression of the same nucleotide sequence of interest in a different type of tissue (e.g., bone). Tissue specificity of a promoter may be evaluated by, for example, operably linking a reporter gene to the promoter sequence to generate a reporter construct, introducing the reporter construct into the genome of an organism such that the reporter construct is integrated into every tissue of the resulting transgenic organism, and detecting the expression of the reporter gene (e.g., detecting mRNA, protein, or the activity of a protein encoded by the reporter gene) in different tissues of the transgenic organism. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or inducible. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap, Plant Mol. Biol. 24:119–127 [1994]) promoters. Such promoters have been used successfully to direct the expression of heterologous nucleic acid sequences in transformed plant tissue.

In contrast, an "inducible" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York [1989] pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6–16.7).

The term "vector" refers to nucleic acid molecules that transfer DNA segment(s) from one cell to another. The term "vehicle" is sometimes used interchangeably with "vector."The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "transgene" refers to a foreign gene that is placed into an organism by the process of transfection. The term "foreign gene" refers to any nucleic acid (e.g., gene sequence) that is introduced into the genome of an organism by experimental manipulations and may include gene sequences found in that organism so long as the introduced gene does not reside in the same location as does the naturally-occurring gene.

The term "transgenic" when used in reference to a host cell or an organism refers to a host cell or an organism that contains at least one heterologous or foreign gene in the host cell or in one or more of cells of the organism.

The term "host cell" refers to any cell capable of replicating and/or transcribing and/or translating a heterologous gene. Thus, a "host cell" refers to any eukaryotic or prokaryotic cell (e.g., bacterial cells such as $E.$ $coli$, yeast cells, mammalian cells, avian cells, amphibian cells, plant cells, fish cells, and insect cells), whether located in vitro or in vivo. For example, host cells may be located in a transgenic animal. In the present invention, it is contemplated that host cells are, for example, osteoblasts, osteocytes, osteoclasts and chondrocytes.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074, 859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. [1989] *Molecular Cloning: A Laboratory Manual*, Cold Spring Harbor Press, NY, pp 9.31–9.58).

The term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. [1989] supra, pp 7.39–7.52).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabeled antibodies.

The term "antigenic determinant" refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences, that are removed from their natural environment, isolated or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution. Compositions comprising polynucleotide sequences encoding mustang (e.g., SEQ ID NO:2) or fragments thereof may be employed as hybridization probes. In this case, the mustang encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "response," when used in reference to an assay, refers to the generation of a detectable signal (e.g., accumulation of reporter protein, increase in ion concentration, accumulation of a detectable chemical product).

The term "sample" is used in its broadest sense. In one sense it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

The term "at least one symptom is reduced" shall be defined as meaning that, after treatment, at least one of any number of symptoms is reduced. The reduction need not be complete. That is, a partial reduction in the symptom is contemplated. Additionally, the symptom need not be reduced permanently. A temporary reduction in at least one symptom is contemplated by the present invention.

The term "subject at risk" shall be defined as a person or patient in whom it is plausible that at least one symptom of a condition of abnormal bone growth, abnormal bone regeneration or abnormal bone repair may occur. Such subjects may, for example, be from families where other members have had such symptoms but the subject has not shown symptoms. Additionally, subjects at risk may be individuals in which there is a genetic history of such symptoms in the individual's family, race, nationality or heritage.

BRIEF DESCRIPTION OF THE DRAWINGS

FIG. 1 shows the nucleotide sequence of the full-length rat MUSTANG cDNA (SEQ ID NO:1. A. The nucleotide sequence of the 82 amino acid open reading frame (ORF) is shown as bold. The stop codon (TGA) is shown as an asterisk (*). The polyadenylation site (AATAAA) (SEQ ID NO:4) and primer sequences used to clone the cDNA are underlined. B. Amino acid comparison of rat MUSTANG (SEQ ID NO:2) with its homologous mouse(SEQ ID NO:5), human (SEQ ID NO:6) and cow (SEQ ID NO:7) sequences with 93%, 88% and 85% homology to rat, respectively. Amino acid substitutions are highlighted in bold. The underlined amino acid sequence indicates the nuclear import signal (PIKKKRPPV)(SEQ ID NO:3).

FIG. 3 shows cDNA microarray analysis. Images of the same area from two microarray filters following hybridization with radioactively labeled RNA obtained from intact bone [FIG. 3A] and PF day 10 [FIG. 3B]. Arrows indicate the varying signal intensity between the same spots on each membrane, indicating differential gene expression.

FIG. 7 shows a cDNA Microarray Analysis. Images derived from the same region of two identical microarray filters following hybridization with radioactively labeled RNA obtained from intact bone [FIG. 7A] and post fracture day 5 callus [FIG. 7B]. Arrows designate the same spot representing MUSTANG with varying intensity (indicating differential expression) between the two filters. As a comparison, another spot corresponding to collagen type I is shown by an arrowhead. Smaller arrows indicate two cDNAs whose expression did not change between intact and PF day 5 callus.

DETAILED DESCRIPTION OF THE PREFERRED EMBODIMENTS

Figure 2:
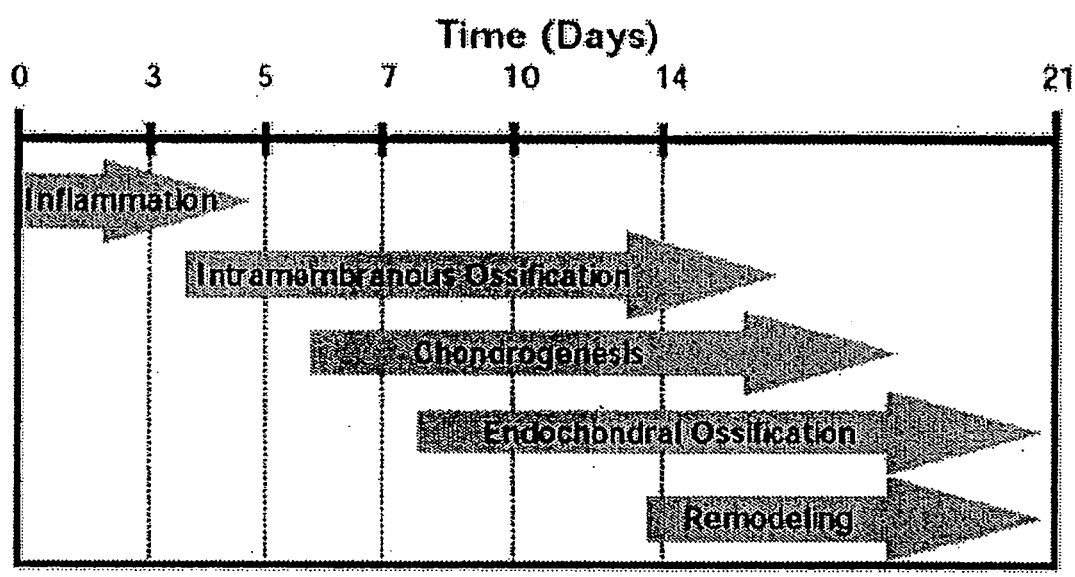
FIG. 2 shows a time line showing the interdependent central physiologic processes occurring during the progression of the healing fracture callus. Each of the arrows indicates the approximate starting time and duration of each process.

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y., which are incorporated herein by reference) which are provided throughout this document. All the information contained therein is incorporated herein by reference.

Oligonucleotides can be synthesized on an Applied BioSystems oligonucleotide synthesizer [for details see Sinha, et al., Nucleic Acids Res. 12:4539 (1984)], according to specifications provided by the manufacturer. Complementary oligonucleotides are annealed by heating them to 90° C. in a solution of 10 mM Tris-HCl buffer (pH 8.0) containing NaCl (200 mM) and then allowing them to cool slowly to room temperature.

I. Exemplary Gene Therapeutic Applications of Mustang

1. The Multicellular Organism

Any multicellular organism into which it may be desirable to introduce exogenous nucleic acid comprising the mustang gene (i.e., SEQ ID NO: 1 or a portion thereof) is a potential subject for the present invention. The multicellular organism may be any animal. The animal is preferably a vertebrate animal, and more preferably a higher vertebrate, i.e., a mammal or bird, the former being especially preferred. Among mammals, preferred subjects are human and other primates, laboratory animals such as mice, rats, rabbits and hamsters, pet animals such as dogs and cats, and farm animals such as horses, cows, goats, pigs and sheep. It will be noted that these animals come from four orders of class Mammalia: Primata, Rodenta, Camivora and Artiodactyla.

2. The Target Cell

The target cells may belong to tissues (including organs) of the organism, including cells belonging to (in the case of an animal) its nervous system (e.g., the brain, spinal cord and peripheral nervous cells), the circulatory system (e.g., the heart, vascular tissue and red and white blood cells), the digestive system (e.g., the stomach and intestines), the respiratory system (e.g., the nose and the lungs), the reproductive system, the endocrine system (the liver, spleen, thyroids, parathyroids), the skin, the muscles, or the connective tissue. In a preferred embodiment, the target cells comprise cells and tissues of the skeletal system (e.g., osteoblasts, osteocytes, chondrocytes, osteoclasts, chondroclasts, osteocytes, hematopoietic marrow cells, synovial cells, and connective tissue fibroblasts).

A useful procedure for gene therapy requires an efficient and relatively non-invasive approach to the introduction of genes of interest into the target cells. Several techniques, employing receptor mediated gene transfer, have been used with some success. Other methods are given in U.S. Pat. Nos. 5,972,900; 5,972,901 and 6,200,801 to Ferkol, et al., and incorporated herein by reference.

In one embodiment, the present invention contemplates the use of the procedures of the above referenced US patents for the incorporation of the gene of the present invention (i.e., SEQ ID NO: 1 or a portion thereof) into the target cells. In brief, this procedure has application to human gene therapy. The major advantages of the method are: (i) the ease of preparation of the DNA complex; (ii) the ability to target genes to specific tissues; (iii) the prolonged expression of the gene in the liver; (iv) the relative safety of the complex, since it is devoid of infectious viral DNA; and (v) the episomal maintenance of the introduced gene.

3. Targeting

A. Generally

"Targeting" is the administration of the compacted nucleic acid in such a manner that it enters the target cells in amounts effective to achieve the intended purpose. In this regard, it should be noted that DNA and RNA are capable of replication in the nucleus of the target cell, and in consequence the ultimate level of the nucleic acid in the cell may increase after uptake. Moreover, if the clinical effect is mediated by a protein expressed by the nucleic acid, it should be noted that the nucleic acid acts as a template, and thus high levels of protein expression can be achieved even if the number of copies of the nucleic acid in the cell is low. Nonetheless, it is desirable to compact high concentrations of DNA to increase the number of target cells which take up the DNA and the number of DNA molecules taken up by each cell.

The route and site of administration may be chosen to enhance targeting. For example, to target muscle cells, intramuscular injection into the muscles of interest would be a logical choice. Lung cells might be targeted by administering the compacted DNA in aerosol form. The vascular endothelial cells could be targeted by coating a balloon catheter with the compacted DNA and mechanically introducing the DNA. To target bone cells, injection into the bones and bone tissues (e.g., cartilage) is contemplated. Other methods of using the nucleotide sequence of the present invention are also contemplated. Examples in the literature include, but are not limited to: U.S. Pat. Nos. 6,426,186, 6,369,027 and 6,521,750, which are herein incorporated by reference.

In some instances, the nucleic acid binding moiety, which maintains the nucleic acid in the compacted state, may also serve as a targeting agent. Polymers of positively charged amino acids are known to act as nuclear localization signals (NLS) in many nuclear proteins. For example, a pSV40-luciferase DNA condensed with poly-L-lysine, was injected in situ into the abdominal muscle of rats. Despite the absence of an explicit target cell binding moiety, a 20-fold higher luciferase activity in rats injected with the complexed DNA than in the rat injected with naked DNA was observed. Nonetheless, in some embodiments, targeting may be improved if a target cell binding moiety is employed.

i. Receptor-Mediated Uncompacted DNA Delivery In Vivo

Receptor-mediated gene transfer has been shown to be successful in introducing transgenes into suitable recipient cells, both in vitro and in vivo. This procedure involves linking the DNA to a polycationic protein (usually poly-L-lysine) containing a covalently attached ligand, which is selected to target a specific receptor on the surface of the tissue of interest. The gene is taken up by the tissue, transported to the nucleus of the cell and expressed for varying times. The overall level of expression of the transgene in the target tissue is dependent on several factors: the stability of the DNA-carrier complex, the presence and number of specific receptors on the surface of the targeted cell, the receptor-carrier ligand interaction, endocytosis and transport of the complex to the nucleus, and the efficiency of gene transcription in the nuclei of the target cells.

Wu, et al., U.S. Pat. No. 5,166,320 (incorporated herein by reference), discloses tissue-specific delivery of DNA using a conjugate of a polynucleic acid binding agent (such as polylysine, polyarginine, polyornithine, histone, avidin, or protamine) and a tissue receptor-specific protein ligand. For example, for targeting liver cells, Wu suggests "asialoglycoprotein (galactose-terminal) ligands."

Wagner, et al., *Proc. Natl. Acad. Sci.*, 88:4255–4259 (1991) and U.S. Pat. No. 5,354,844 (incorporated herein by reference) disclose complexing a transferrin-polylysine conjugate with DNA for delivering DNA to cells via receptor mediated endocytosis. Wagner, et al., teach that it is important that there be sufficient polycation in the mixture to ensure compaction of plasmid DNA into toroidal structures of 80–100 nm diameter, which, they speculate, facilitate the endocytic event.

ii. Direct Injection of Naked, Uncompacted DNA

The possibility of detecting gene expression by directly injecting naked DNA into animal tissues was demonstrated first by Dubenski et al., *Proc. Nat. Acad. Sci. USA*, 81:7529–33 (1984), who showed that viral or plasmid DNA injected into the liver or spleen of mice was expressed at detectable levels. The DNA was precipitated using calcium phosphate and injected together with hyaluronidase and collagenase. The transfected gene was shown to replicate in the liver of the host animal. Benvenisty and Reshef, *Proc. Nat. Acad. Sci. USA*, 83:9551–55 (1986) injected calcium phosphate precipitated DNA intraperitoneally into newborn rats and noted gene expression in the livers of the animals 48 hours after transfection. In 1990, Wolff, et al., *Science*, 247:1456–68 (1990), reported that the direct injection of DNA or RNA expression vectors into the muscle of mice resulted in the detectable expression of the genes for periods for up to 2 months. This technique has been extended by Acsadi, et al., *New Biologist*, 3:71–81 (1991) to include direct injection of naked DNA into rat hearts; the injected genes were expressed in the heart of the animals for up to 25 days. Other genes, including the gene for dystrophin have been injected into the muscle of mice using this technique. This procedure forms the base of a broad approach for the generation of immune response in an animal by the administration of a gene by direct injection into the target tissue. The gene is transiently expressed, producing a specific antigen. (See Donnelly, et al., *The Immunologist*, 21, pp. 20–26 (1994) for a recent review). However, the DNA used in these experiments has not been modified or compacted to improve its survival in the cell, its uptake into the nucleus or its rate of transcription in the nucleus of the target cells.

B. Use of a Target Binding Moiety (TBM)

If a TBM is used, it must bind specifically to an accessible structure (the "receptor") of the intended target cells. It is not necessary that it be absolutely specific for those cells, however, it must be sufficiently specific for the conjugate to be therapeutically effective. Preferably, its cross-reactivity with other cells is less than 25%, more preferably less than 10% and most preferably less than 5%.

There is no absolute minimum affinity which the TBM must have for an accessible structure of the target cell; however, the higher the affinity, the better. Preferably, the affinity is at least $10^3$ liters/mole, more preferably, at least $10^6$ liters/mole.

The TBM may be an antibody (or a specifically binding fragment of an antibody, such as an Fab, Fab, $V_M$, $V_L$ or CDR) which binds specifically to an epitope on the surface of the target cell. In the case of the present invention, it is contemplated that an antibody is made against the Mustang protein (i.e., SEQ ID NO: 2) or antigenic portions thereof. Methods for raising antibodies against cells, cell membranes, isolated cell surface antigens or other proteins are known in the art. Furthermore, the TBM may comprise a single-chain Fv which binds specifically to an epitope on the surface of the target cell. The single-chain Fv may comprise a fusion protein with a NABM or a therapeutic protein sequence (e.g, an enzyme, cytokine, protein antibiotic, etc.).

The TBM may be a lectin, for which there is a cognate carbohydrate structure on the cell surface.

The target binding moiety may be a ligand which is specifically bound by a receptor carried by the target cells.

One class of ligands of interest are carbohydrates, especially mono- and oligosaccharides. Suitable ligands include galactose, lactose and mannose.

Another class of ligands of interest are peptides (which here includes proteins), such as insulin, epidermal growth factor(s), tumor necrosis factor, prolactin, chorionic gonadotropin, FSH, LH, glucagon, lactoferrin, transferrin, apolipoprotein E, gp120 and albumin.

Although the preferred binding moieties are found on bone and other cells of the skeletal system, the invention is not limited to those cells. The present invention contemplates that the protein of SEQ ID NO: 2 may be useful as a ligand for other cells. The following table lists exemplary target binding moieties for various classes of target cells:

| Target Cells | Target Binding Moiety |
|---|---|
| bone cells | osteopontin, CD44 |
| liver cells | galactose |
| Kupffer cells | mannose |
| macrophages | mannose |
| lung, liver, intestine | Fab fragment vs. polymeric immunoglobulin receptor (pIg R) |
| adipose tissue, | insulin |
| lymphocytes | Fab fragment vs. CD4 or gp120 |
| enterocyte | Vitamin B12 |
| muscle | insulin |
| fibroblasts | mannose-6-phosphate |
| nerve cells | Apolipoprotein E |

The target binding moiety may be encompassed with a larger peptide or protein. For example, the present invention provides peptides comprising the hyaluronan CD44 binding domain (Noonan K J, et al., "Spatial distribution of CD44 and hyaluronan in the proximal tibia of the growing rat." *J. Orthop Res* 14:573–81, 1996). The present invention further contemplates the production of retroviral particles comprising modified (i.e., chimeric) envelope proteins containing protein sequences comprising a target binding moiety capable of binding to osteopontin or CD44 (or any other desired receptor). Retrovirus particles bearing these modified envelope proteins may be used to deliver genes of interest to cells expressing, for example, osteopontin or CD44. Retroviral particles bearing chimeric proteins containing peptide ligands and a portion of the envelope (env) protein of retroviruses (e.g., ecotropic Moloney murine leukemia virus or avian retroviruses) have been shown to be capable of binding to cells expressing the cognate receptor [Kasahara et al. (1994) *Science* 266:1373 and Valsesia-Wittmann et al. (1994) *J. Virol.* 68:4609]

The use of a target binding moiety is not strictly necessary in the case of direct injection of the NABM/NA (nucleic acid binding moiety/nucleic acid) condensed complex. The target cell in this case is passively accessible to the NABM/NA condensed complex by the injection of the complex to the vicinity of the target cell.

C. Liposome-Mediated Gene Transfer

The possibility of detecting gene expression by encapsulating DNA into a liposome (body contained by a lipid bilayer) using various lipid and solvent conditions, and injecting the liposome into animal tissues, has been demonstrated. However, despite the potential of this technique for a variety of biological systems, the DNA used in these experiments has not been modified or compacted to improve its survival in the cell, its uptake into the nucleus or its rate of transcription in the nucleus of the target cells. Thus, these procedures have usually resulted in only transient expression of the gene carried by the liposome.

Cationic lipids have been successfully used to transfer DNA. The cationic component of such lipids can compact DNA in solution. This method has been shown to result in heavily aggregated DNA complexes that, when used for transfecting the DNA in vitro, results in increased efficiency of gene transfer and expression (relative to naked DNA). Although the formation of these complexes can promote gene transfer in vitro, the injection of such complexes in vivo does not always result in long lasting and efficient gene transfer.

The condensation procedures incorporated into the present invention by reference (see, U.S. Pat. Nos. 5,972,900; 5,972,901 and 6,200,801 to Ferkol, et al.,) provide structural features to the DNA/cationic lipid complex that will make it more amenable to prolonged in vivo expression. The combination of such methods could be accomplished by either of two procedures:

1. Formation of condensed DNA complex that is later encapsulated using neutral lipids into liposome bodies, or
2. Using the procedure described in this patent, the formation of highly condensed unimolecular DNA complexes upon condensation with cationic lipids could be accomplished. These complexes should provide a higher efficiency of gene transfer into tissues of animals in vivo.

The procedure of the present invention for the condensation of DNA, if coupled to the encapsulation of the resulting compacted DNA into a liposome body, could provide a variety of advantages for transfection into animals:

1. The liposome promotes the passive fusion with the lipid bilayer of the cytoplasmic membrane of mammalian cells in tissues.
2. The condensed DNA could then transfer the genetic information with a higher efficiency through the cell compartments to the nucleus for its expression.
3. Condensed DNA could be protected against degradation inside the cell, thus augmenting the duration of the expression of the newly introduced gene.
4. Possible immunological response to the polycation condensed DNA could be avoided by the encapsulation with the immunologically inert lipid bilayer.

D. The Nucleic Acid Binding Moiety

Any substance which binds reversibly to a nucleic acid may serve as the nucleic acid binding moiety (NABM), provided that (1) it binds sufficiently strongly and specifically to the nucleic acid to retain it until the conjugate reaches and enters the target cell, and does not, through its binding, substantially damage or alter the nucleic acid and (2) it reduces the interactions between the nucleic acid and the solvent, and thereby permits condensation to occur. The ultimate criterion is one of therapeutic effectiveness of the conjugate.

Preferably, the NABM is a polycation. Its positively charged groups bind ionically to the negatively charged DNA, and the resulting charge neutralization reduces DNA-solvent interactions. A preferred polycation is polylysine. Other potential nucleic acid binding moieties include Arg-Lys mixed polymers, polyarginine, polyomithine, histones, avidin, and protamines.

i. The Nucleic Acid

Basic procedures for constructing recombinant DNA and RNA molecules in accordance with the present invention are disclosed by Sambrook, J. et al., In: *Molecular Cloning: A*

*Laboratory Manual*, Second Edition, Cold Spring Harbor Press, Cold Spring Harbor, N.Y. (1989), which reference is herein incorporated by reference.

The nucleic acid may be a DNA, RNA, or a DNA or RNA derivative such as a derivative resistant to degradation in vivo, as discussed below. Within this specification, references to DNA apply, *mutatis mutandis*, to other nucleic acids as well, unless clearly forbidden by the context. The nucleic acid may be single or double stranded. It is preferably of 10 to 1,000,000 bases (or base pairs), more preferably 100 to 100,000, and the bases may be same or different. The bases may be the "normal" bases adenine (A), guanine (G), thymidine (T), cytosine (C) and uracil (U), or abnormal bases such as those listed in 37 CFR § 1.822 (p) (1). The nucleic acid may be prepared by any desired procedure.

In a preferred embodiment, the nucleic acid comprises an expressible gene which is functional in the target cell. For example, the gene may encode coagulation factors, (such as Factor IX), enzymes involved in specific metabolic defects, (such as urea cycle enzymes, especially ornithine transcarbamylase, argininosuccinate synthase, and carbamyl phosphate synthase); receptors, (e.g., LDL receptor); toxins; thymidine kinase to ablate specific cells or tissues; ion channels (e.g., chloride channel of cystic fibrosis); membrane transporters (e.g., glucose transporter); and cytoskeletal proteins, (e.g., dystrophin). In a preferred embodiment, the expressible gene is mustang (i.e., SEQ ID NO: 1). The gene may be of synthetic, cDNA or genomic origin, or a combination thereof. The gene may be one which occurs in nature, a non-naturally occurring gene which nonetheless encodes a naturally occurring polypeptide, or a gene which encodes a recognizable mutant of such a polypeptide. It may also encode an mRNA which will be "antisense" to a DNA found or an mRNA normally transcribed in the host cell, but which antisense RNA is not itself translatable into a functional protein.

For the gene to be expressible, the coding sequence must be operably linked to a promoter sequence functional in the target cell. Two DNA sequences (such as a promoter region sequence and a coding sequence) are said to be operably linked if the nature of the linkage between the two DNA sequences does not (1) result in the introduction of a frame-shift mutation in the region sequence to direct the transcription of the desired gene sequence, or (2) interfere with the ability of the gene sequence to be transcribed by the promoter region sequence. A promoter region would be operably linked to a DNA sequence if the promoter were capable of effecting transcription of that DNA sequence. In order to be "operably linked" it is not necessary that two sequences be immediately adjacent to one another. A nucleic acid molecule, such as DNA, is said to be "capable of expressing" a mRNA if it contains nucleotide sequences which contain transcriptional regulatory information and such sequences are "operably linked" to nucleotide sequences which encode the RNA. The precise nature of the regulatory regions needed for gene expression may vary from organism to organism, but in general include a promoter which directs the initiation of RNA transcription. Such regions may include those 5'-non-coding sequences involved with initiation of transcription such as the TATA box.

If desired, the non-coding region 3' to the gene sequence coding for the desired RNA product may be obtained. This region may be retained for its transcriptional termination regulatory sequences, such as those which provide for termination and polyadenylation. Thus, by retaining the 3'-region naturally contiguous to the coding sequence, the transcriptional termination signals may be provided. Where the transcriptional termination signals are not satisfactorily functional in the expression host cell, then a 3' region functional in the host cell may be substituted.

Promoters specific for bone and other connective tissue cells are listed elsewhere in this application. It is also contemplated that the promoter may be an "ubiquitous" promoter active in essentially all cells of the host organism, e.g., for mammals, the beta-actin promoter, or it may be a promoter whose expression is more or less specific to the target cells. Generally speaking, the latter is preferred. A promoter native to a gene which is naturally expressed in the target cell may be used for this purpose, e.g., the PEPCK (phosphoenol pyruvate carboxykinase) promoter for expression in mammalian liver cells. Other suitable promoters include albumin, metallothionein, surfactant, apoe, pyruvate kinase, LDL receptor HMG CoA reductase or any promoter which has been isolated, cloned and shown to have an appropriate pattern of tissue specific expression and regulation by factors (hormones, diet, heavy metals, etc.) required to control the transcription of the gene in the target tissue. In addition, a broad variety of viral promoters can be used; these include MMTV, SV-40 and CMV. An "expression vector" is a vector which (due to the presence of appropriate transcriptional and/or translational control sequences) is capable of expressing a DNA (or cDNA) molecule which has been cloned into the vector and of thereby producing an RNA or protein product. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, when a eukaryotic expression vector is employed, then the appropriate host cell would be any eukaryotic cell capable of expressing the cloned sequences.

In addition to or instead of an expressible gene, the nucleic acid may comprise sequences homologous to genetic material of the target cell (e.g., a mutant version of the mustang gene), whereby it may insert itself ("integrate") into the genome by homologous recombination, thereby displacing a coding or control sequence of a gene, or deleting a gene altogether.

In another embodiment, the nucleic acid molecule is "antisense" to a genomic or other DNA sequence of the target organism (including viruses and other pathogens) or to a messenger RNA transcribed in cells of the organisms, which hybridizes sufficiently thereto to inhibit the transcription of the target genomic DNA or the translation of the target messenger RNA. The efficiency of such hybridization is a function of the length and structure of the hybridizing sequences. The longer the sequence and the closer the complementarily to perfection, the stronger the interaction. As the number of base pair mismatches increases, the hybridization efficiency will fall off. Furthermore, the GC content of the packaging sequence DNA or the antisense RNA will also affect the hybridization efficiency due to the additional hydrogen bond present in a GC base pair compared to an AT (or AU) base pair. Thus, a target sequence richer in GC content is preferable as a target.

It is desirable to avoid antisense sequences which would form secondary structure due to intramolecular hybridization, since this would render the antisense nucleic acid less active or inactive for its intended purpose. One of ordinary skill in the art will readily appreciate whether a sequence has a tendency to form a secondary structure. Secondary structures may be avoided by selecting a different target sequence.

An oligonucleotide, between about 15 and about 100 bases in length and complementary to the target sequence may be synthesized from natural mononucleosides or, alternatively, from mononucleosides having substitutions at the non-bridging phosphorous bound oxygens. A preferred analogue is a methylphosphonate analogue of the naturally occurring mononucleosides. More generally, the mononucleoside analogue is any analogue whose use results in oligonucleotides which have the advantages of (a) an improved ability to diffuse through cell membranes and/or (b) resistance to nuclease digestion within the body of a subject (Miller, P. S. et al., *Biochemistry* 20:1874–1880 (1981)). Such nucleoside analogues are well-known in the art. The nucleic acid molecule may be an analogue of DNA or RNA. The present invention is not limited to use of any particular DNA or RNA analogue, provided it is capable of fulfilling its therapeutic purpose, has adequate resistance to nucleases, and adequate bioavailability and cell take-up. DNA or RNA may be made more resistant to in vivo degradation by enzymes, e.g., nucleases, by modifying internucleoside linkages (e.g., methylphosphonates or phosphorothioates) or by incorporating modified nucleosides (e.g., 2'-0-methylribose or 1'-alpha-anomers). The entire nucleic acid molecule may be formed of such modified linkages, or only certain portions, such as the 5' and 3' ends, may be so affected, thereby providing resistance to exonucleases.

Nucleic acid molecules suitable for use in the present invention thus include but are not limited to dideoxyribonucleoside methylphosphonates, see Mill, et al., Biochemistry, 18:5134–43 (1979), oligodeoxynucleotide phosphorothioates, see Matsukura, et al., *Proc. Nat. Acad. Sci.*, 84:7706–10 (1987), oligodeoxynucleotides covalently linked to an intercalating agent, see Zerial, et al., Nucleic Acids Res., 15:9909–19 (1987), oligodeoxynucleotide conjugated with poly(L-lysine), see Leonetti, et al., *Gene*, 72:32–33 (1988), and carbamate-linked oligomers assembled from ribose-derived subunits, see Summerton, J., Antisense Nucleic Acids Conference, 37:44 (New York 1989).

ii. Compaction of the Nucleic Acid

In one embodiment, it is desirable that the complex of the nucleic acid and the nucleic acid binding moiety be compacted to a particle size which is sufficiently small to achieve uptake by receptor mediated endocytosis, passive internalization, receptor-mediated membrane permeabilization, or other applicable mechanisms. Desirably, the complex of the compacted nucleic acid, the target binding moiety, and the nucleic acid binding moiety is small, e.g., less than 100 nm, because the sinusoidal capillary systems of the lung and spleen will trap aggregates of that size, and more preferably less than 80 or 90 nm, as that is the typical internal diameter of coated-pit endocytic vesicles. Since complexes larger than 30 nm may be susceptible to nonspecific take up by macrophages in the spleen and liver, the conjugate is preferably also smaller than 30 nm.

The present invention calls for the complex of the nucleic acid and the nucleic acid-binding carrier to be compacted without causing aggregation or precipitation, and preferably to a condensed state. For the purpose of the present invention, it is helpful to characterize DNA as having one of the following states: normal (uncondensed); condensed; relaxed; uni-aggregated (clusters of unimolecular toroids); multi-aggregated (clusters of multimolecular toroids); and precipitated. These states are defined in terms of their appearance under electron microscopy.

Condensed DNA is in a state in which interaction with the solvent is minimal and therefore the DNA is in the form of isolated spheres or toroids. It is not fibrous to an appreciable degree. Relaxed DNA, typically formed by dissociation of polycation from the DNA, forms fibers. Aggregated DNA forms clumped or multimolecular toroids.

The theoretical size of a unimolecular DNA complex can be calculated by the formulae known to those practiced in the art (see, for example, Table 106 in U.S. Pat. No. 6,200,801 to Ferkol, et al.). Preferably, the complexes of this invention have a diameter which is less than double the size calculated by one or both of these formulae. Larger complexes are likely to correspond to multimolecularly aggregated DNA.

DNA can be compacted to a condensed state by neutralizing its charge, e.g., by addition of a polycation, or otherwise reducing its interactions with solvent. However, the polycation can cause aggregation or precipitation of the DNA if a chaotropic agent is not employed to prevent it. Compaction therefore can be accomplished by judicious use of both the polycation (to condense the DNA) and (as needed) of a chaotropic agent (to prevent aggregation or precipitation).

Overuse of the chaotropic agent can, however, result in relaxation of the DNA. Preferably, the complex has a unaggregated, unimolecular toroid structure condensed to smaller than 23 nm in diameter; the degree of compaction may be determined by electron microscopy. For example, a complex of the PEPCK-hFIX gene with galactosylated polylysine has been compacted to a unimolecular toroid with a mean diameter of about 12 nm.

The term "unimolecular toroid" indicates that the toroid contains only one nucleic acid molecule; the toroid may contain many carrier (e.g., galactosylated poly-Lys) molecules. A typical ratio is one DNA molecule to about 100 carrier molecules, per "unimolecular" toroid. Alternatively, and perhaps more precisely, this structure may be referred to as a mono-nucleic acid toroid. Unimolecular and multimolecular toroids (the latter each contain more than one DNA molecule) may be distinguished by the different size of each of the complexes when viewed by the electron microscope, indicating the multi- or unimolecular (counting only the DNA molecules) composition of the toroids.

Other techniques have been used to identify structural changes in the DNA upon poly-L-lysine binding. The first of these is the spectrophotometric determination of the turbidity in the solution using the absorbance at 400 nm. Turbidity is primarily an indicator of aggregation. Aggregation is confirmed by a circular dichroism (CD) value greater than 0 at wavelengths from 300 to 340 nm.

Adding the poly-L-lysine to the DNA solution at different starting concentrations of NaCl increases turbidity. Turbidity increases as the initial concentration of salt is increased (this could be easily confirmed by eye), indicating that the condensation of the DNA complex at lower ionic strength results in a suspension of particles composed of unimolecular DNA-poly-L-lysine complexes interacting with each other. We noted that the solutions of DNA condensed at lower salt concentration were clear, with the presence of particulate matter in suspension. Solutions containing the DNA complex with different degrees of turbidity were analyzed by EM to visualize the DNA structures formed in each situation. Appropriately condensed, unimolecular DNA complexes were found with both clear and slightly turbid solutions. This was not true for the condensation of DNA complexes at initial low ionic strength where we noted minimal absorbance at 400 nm because the solutions containing particles in suspension did not absorb at 400 nm. However, when these solutions were analyzed using EM, the expected transitional structures were noted. When the particles in suspension became totally dispersed, the structures identified by EM were essentially identical to condensed unimolecular DNA complexes. Thus, turbidity of the solution containing the DNA complexes is dependent on the initial concentration of salt used for condensation of the complex. Although the mechanisms responsible for the observed differences in the condensation of DNA at initial low and high ionic strength is not clear, we adapted our protocol to appropriately condense DNA, avoiding the formation of turbid solutions.

A more reliable technique for diagnosing the structural transition of DNA-poly-L-lysine complexes in solution is the absorbance of the condensing complex at 260 nm as the concentration of NaCl increases. The uni-aggregated DNA complex in suspension has only 10–30% of the expected absorbance because the particulate matter does not absorb at 260 nm. The addition of NaCl disperses the uni-aggregated DNA complex in suspension which results in the observed steep increase in the absorbance. At this point the solution was clear and there were no visible particulate structures in suspension. This feature of the DNA-poly-L-lysine condensation clearly correlates with the transitional structures mentioned above. At a concentration of NaCl which causes a steep increase in the absorbance at 260 nm, we observed unaggregated, condensed complexes by EM; before this critical concentration of NaCl was attained, the DNA complex appear aggregated and at higher NaCl concentrations the DNA complex was relaxed. A second transition in absorbance at 260 nm, as a result of the relaxation of the condensed DNA complex that was in suspension, indicates the full solubilization of the DNA complex.

Circular dichroism (CD) can be used to monitor the condensation of DNA. When the spectrum is identical to that of DNA alone, then the DNA complex is assumed to be correctly compacted, i.e., into unimolecular complexes. In another words, the positive spectrum at 220 nm is quantitatively similar to the 220 nm spectrum of DNA alone, and the cross-over (the wavelength at which the spectrum of the complex crosses the 0 point) is essentially identical to that of DNA alone. When the DNA aggregates into multimolecular complexes, the positive spectrum at 270 nm is inverted into a negative spectrum at that wavelength (this is called psi-DNA structure or ψ-DNA).

It should be noted that any other techniques which are capable of identifying condensed DNA complexes may be used instead of or in combination with those discussed above.

To compact the nucleic acid, the carrier is added to the nucleic acid solution, whereby the carrier disrupts the nucleic acid:solvent interactions allowing the nucleic acid to condense. Preferably, at least the turbidity of the solution is monitored as the carrier is added, so that a change in state is promptly detected. Once turbidity appears, the state of the DNA may be further analyzed by CD spectroscopy to determine whether the DNA is in the condensed or the aggregated state. (Precipitation should also be detectable with the naked eye.) Preferably, the carrier is added sufficiently slowly to the nucleic acid solution so that precipitation and aggregation are minimized. If precipitation or aggregation occur, a chaotropic salt should be added slowly, and the result again examined by CD spectroscopy. The preferred salt is NaCl. Other chaotropic salts can be used as long as they are tolerated by the animal (or cells) to which they will be administered. Suitable agents include Sodium sulfate ($Na_2SO_4$), Lithium sulfate ($Li_2SO_4$), Ammonium sulfate (($NH_4$)$_2SO_4$, Potassium sulfate ($K_2SO_4$), Magnesium sulfate ($MgSO_4$), Potassium phosphate ($KH_2PO_4$), Sodium phosphate ($NaH_2PO_4$), Ammonium phosphate ($NH_4H_2PO_4$), Magnesium phosphate ($MgHPO_4$), Magnesium chloride ($MgCl_2$), Lithium chloride (LiCl), Sodium chloride (NaCl), Potassium chloride (KCl), Cesium chloride (CaCl), Ammonium acetate, Potassium acetate, Sodium acetate, Sodium fluoride (NaF), Potassium fluoride (KF), Tetramethyl ammonium chloride (TMA-Cl), Tetrabutylammonium chloride (TBA-Cl), Triethylammoniym chloride (TEA-Cl) and Methyltriethylammonium chloride (MTEA-Cl).

Variables that affect condensation of DNA in vitro have been investigated and the functional relevance of these parameters for efficient delivery of DNA complexes into animals by receptor-mediated endocytosis. A strong correlation between the ionic strength at which the condensed DNA-poly-L-lysine complex remains stable in solution and the concentration of DNA was noted. These experiments were performed using a 4.5 kb plasmid containing the promoter from the gene for PEPCK linked to the structural gene for hFIX, using a ratio of DNA to poly-L-lysine that resulted in a 1 to 1 ratio of negative to positive charges in solution. The variation in the final concentration of NaCl necessary to solubilize the particles is a logarithmic function of DNA concentration, in which the condensation of highly concentrated DNA-poly-L-lysine complexes occurs with only a slight increase in ionic strength. This physical characteristic of DNA condensation has clear advantages for the delivery of the DNA particles to tissues of adult animals in vivo since it has little effect on the ionic load in the animal's blood.

The linear fit of the data using the least square method is described by the following function:

$$\log_{10}(NaCl, mM) = b0*(DNA, \mu M\ Phosphate) + b1$$
$$r2 = 0.97$$

where $b0 = 2.52 \times 10\ E{-}3$, $b1 = 0.577$

It was observed that there were variations in the function described by the above equation when different DNA plasmids and different DNA preparations during the condensation process were used. These differences are probably related to the variation in the affinity of poly-L-lysine for DNA of different sources and compositions. For maximum binding affinity we generally use DNA precipitated twice with sodium acetate and 2.5 volumes of −40° C. ethanol. No apparent difference in binding affinity of poly-L-lysine for DNA of different forms (i.e., supercoiled, nicked and linear) and for DNA extracted using anionic exchange chromatography or cesium chloride gradient centrifugation was found. This may indicate the presence of a contaminant in the DNA preparations from different sources which has poly-L-lysine binding activity, that is eliminated by sequential DNA precipitation.

The effect of the length of the poly-L-lysine on the concentration of NaCl necessary for the effective condensation of DNA has been investigated. The correlation between these variables was assessed using a fixed concentration of DNA from different sources. A broad range of poly-L-lysine lengths; essentially the sizes of poly-L-lysine available commercially has been used. However, the length of the poly-L-lysine in an average of various sizes of the protein as determined by low-angle light scattering analysis of individual lots of chemically synthesized poly-L-lysine. The actual distribution of sizes within each sample varies from 60 to 80% of the material being distributed, which is +/−20% from the average size. This broad distribution within a single size is a source of error in our determinations. Nevertheless, there is a clear correlation between the length of the poly-L-lysine and the necessary concentration of NaCl needed for the condensation of the DNA complex in solution. This correlation is a linear function of poly-L-lysine length up to a size of 150 lysine residues, after which the function reaches saturation and there is no increase in the concentration of NaCl needed for the condensation of DNA with longer poly-L-lysine. These data are consistent with a cooperative binding between the poly-L-lysine and the DNA phosphate backbone. Thus, by reducing the length of the poly-L-lysine molecules used to condensed the DNA the solution of DNA complex injected into the animals will be less hypertonic. It is also important to consider the dilution of the DNA complex in the blood of the animal to evaluate the functional significance of these changes in ionic strength on the efficiency of this method for gene therapy. Rats have been injected with DNA complexes containing longer range of poly-L-lysine lengths and rabbits with the shorter range of sizes of poly-L-lysine, and noted positive and persistent expression of the transfected genes in both cases.

The preferred minimum initial salt concentration is dependent on the compaction activity of the carrier and the chaotropic activity of the salt. If the NABM were $(Lys)_8$, or $(Lys)_{27}$, the initial NaCl concentration could be zero. With longer polyLys chains, however, in the absence of NaCl, precipitation would be immediate. With $(Lys)_{50}$, the initial NaCl concentration is preferably be at least about 300 mM. Nonetheless, if the TBM is a protein that affects the condensation, the initial salt concentration could be as low as zero.

The carrier may be added continuously, or in small discrete steps. One may begin with a higher flow rate, or larger aliquots, and reduce the flow rate or aliquot size as the desired endpoint of the reaction is neared. Typically 0.1 to 10% of the carrier solution is added at a time to the DNA solution. Each addition is preferably made every 2 seconds to 2 minutes, with constant vortexing. However, longer settlement times may be allowed.

In one embodiment, a nucleic acid, contained in a salt solution, which is preferably at least 0.5 M, but less than 1.5 M NaCl, is mixed with poly-L-lysine (109 lysines) containing the covalently linked target cell binding moiety (for example, galactose), which is contained in a solution of NaCl at the same concentration (e.g., 0.5 to 1.5 M NaCl). Preferably, the molar ratio of nucleic acid phosphate group to positively charged group of the DNA binding moiety is in the range of 4:1 to 1:4, and more preferably is about 1.5:1.

iii. The Conjugation

In the embodiments relying on a target-binding carrier molecule, the nucleic acid binding moiety will be conjugated, covalently or noncovalently, directly or indirectly, to the target cell binding moiety. The conjugation may be performed after, or, more usually before, the loading of the nucleic acid binding moiety with the nucleic acid of interest. Either way, the conjugation should not substantially interfere with the binding of the nucleic acid to the nucleic acid binding moiety, or, for that matter, with the ability of the target cell binding moiety to bind to the target cell.

2. Pharmaceutical Compositions and Methods

The compacted nucleic acid, optionally conjugated with a TBM, may be admixed with a pharmaceutically acceptable excipient (i.e., carrier) for administration to a human or other animal subject. It will be appreciated that it is possible for a DNA solution to contain both condensed DNA and relaxed DNA. The compositions of this invention preferably are sufficiently rich in condensed complexes so that the absorbance at 260 nm is less than 50% that of naked DNA of equal concentration. Condensed DNA usually has an absorbance of 20–30% and relaxed DNA 80–100% that of naked DNA.

The administration may be by any suitable route of administration. The dosage form must be appropriate for that route. Suitable routes of administration and dosage forms include intravascular (injectable solution), subcutaneous (injectable solution, slow-release implant), topical (ointment, salve, cream), and oral (solution, tablet, capsule). With some routes of administration, the dosage form must be formulated to protect the conjugate from degradation, e.g., by inclusion of a protective coating or of a nuclease inhibitor.

The dosage may be determined by systematic testing of alternative doses, as is conventional in the art.

Rats (200–300 g) tolerate as much as 600 μg doses of a DNA complex without any apparent ill effects on growth or health. Mice (25 g) have been injected with 150 μg of that DNA complex without any apparent problem.

In humans, a typical trial dose would be 60–120 mg of DNA; if this dose is too low to be effective or so high as to be toxic, it may be increased, or decreased, respectively, in a systematic manner, until a suitable dose is identified.

For short life span cells, e.g., macrophages, a typical dosing schedule might be one dose every two weeks. For long life span cells, e.g., hepatocytes, one dose every two months might be preferable.

Adjuvants may be used to decrease the size of the DNA complex (e.g., 2–10 mM MgCl), to increase its stability (e.g., sucrose, dextrose, glycerol), or to improve delivery efficiency (e.g., lysosomotropic agents such as chloroquine and monensine). The complexes may be enclosed in a liposome to protect them and to facilitate their entry into the target cell (by fusion of the liposome with the cell membrane).

II. Exemplary Screening Assays for Mustang

The compounds of the present invention may also be used for, e.g., screening assays. Assays for detecting the ability of agents to inhibit or enhance Mustang-mediated processes provide for facile high-throughput screening of agent banks (e.g., compound libraries, peptide libraries, and the like) to identify, for example, antagonists or agonists. Such Mustang (i.e., SEQ ID NO: 2) antagonists and agonists may be further developed as potential therapeutics and diagnostic or prognostic tools for diverse types of cancers, autoimmune diseases and hereditary diseases.

1. Screens to Identify Agonists of Antagonists of Mustang

There are several different approaches contemplated by the present invention to confirm the ability of small molecules to specifically inhibit or enhance the function of Mustang. One approach is to transfect expression constructs specific for the invention into cells and measure changes in the rate of various physiological processes such as growth and apoptosis as compared to controls transfected with empty expression constructs after the cells have been exposed to the compound suspected of modulating Mustang activity. Cells may be transiently transfected or stably transfected with the construct under control of an inducible promoter. Furthermore, transgenic animal could be produced allowing for in vivo assays to be conducted.

A. In vitro Assays i. Transfection Assays

Transfection assays allow for a great deal of flexibility in assay development. The wide range of commercially available transfection vectors will permit the expression of the invention in an extensive number of cell types. In one preferred embodiment, cells would be transiently transfected with the invention in an expression construct that included an inducible promoter allowing for the initiation of translation and transcription when needed. Cells would be exposed to various agents suspected of modulating mustang gene expression (i.e., SEQ ID NO: 1) and/or Mustang peptide activity (i.e., SEQ ID NO: 2). Rates of various physiological processes could be measured by methods know to those practiced in the art (e.g., various growth assays and apoptosis assays as well as measuring the increase or decrease of gene expression, peptide phosphorylation, etc.

In another preferred embodiment stably transfected cells lines would be developed. The use of an inducible promoter would be utilized in these systems. Screening assays for compounds suspected of modulating mustang expression or Mustang activity would be conducted in the same manner as with the transient transfection assays. Using stably transfected cell lines would allow for greater consistency between experiments and allow for inter-experimental comparisons.

B. In Vivo Assays i. Transgenic Animal Assays

In one embodiment transgenic animals will be constructed using standard protocols know to those practiced in the art. The generation of transgenic animals will allow for the investigation of diseases for which the mutated forms of Mustang may provide the means for determining the physiology of the disease or its treatment as well as for creating "knock out" animals (i.e., animals in which the mustang gene has been made non-functional or has a reduced function.

2. Screens to Identify Mustang Interactive Molecules

A. In Vitro Assays

There are several different approaches to identifying Mustang interactive molecules. The invention makes it possible to delineate molecules that may interact with Mustang. Techniques that may be used are, but not limited to, immunoprecipitation of Mustang with antibodies generated to the transcription product of the invention. This would also isolate any associated bound proteins. Another method is to generate fusion proteins containing the Mustang connected to a generally recognized pull-down protein such as glutathione S-transferase. Bound proteins can then be eluded and analyzed. The Mustang fusion proteins would allow the identification of proteins that associated with Mustang molecules. Such proteins may function in the down regulation of Mustang signaling or other Mustang induced or regulated physiological processes.

i. Immunoprecipitation

After the generation of antibodies to Mustang, cells expressing the transfected Mustang are lysed and then incubated with one of the antibodies. Antibodies with the bound Mustang and any associated proteins can then be pulled down with protein-A Sepharose or protein-G Sepharose beads.

ii. Fusion Protein Pull-Down

A method similar to immunoprecipitation is to construct fusion proteins of Mustang and glutathione S-transferase (GST). The GST-Mustang fusion protein is then incubated with cell extracts and then removed with glutathione Sepharose beads. Any bound, Mustang-associated proteins are then characterized.

B. In Vivo Assays i. Yeast Two-Hybrid System

The yeast two-hybrid system that identifies the interaction between two proteins by reconstructing active transcription factor dimers. The dimers are formed between two fusion proteins, one of which contains a DNA-binding domain (DB) fused to the first protein of interest (DB-X) and the other, an activation domain (AD) fused to the second protein of interest (AD-Y). The DB-X:AD-Y interaction reconstitutes a functional transcription factor that activates chromosomally-integrated reporter genes driven by promoters containing the relevant DB binding sites. Large cDNA libraries can be easily screened with the yeast-two hybrid system. Yeast cDNA libraries are commercially available. Standard molecular biological techniques can be employed to isolate and characterize the interacting protein. See, e.g., Fields, S and O. Song, "A novel Genetic System to Detect Protein-Protein Interactions" *Nature* 340:245–246, 1989 and U.S. Pat. Nos. 5,283,173; 5,468,614 and 5,667,973, all of which are incorporated herein by reference.

3. Screens to Identify Mustang Homologs

Standard molecular biological techniques can be used to identify Mustang homologs in humans or other species. For example, preferred embodiments may included, but are not limited to, DNA-DNA hybridization techniques (e.g. Southern blots) and DNA-RNA hybridization techniques (e.g. Northern blots). Additional techniques may include, for example, immunoscreening of proteins made from library stocks by antibodies generated from the invention.

4. Therapeutic Uses for Mustang Gene and Peptide Products

The compositions of the present invention lend themselfs to a multitude of uses in both humans and other animals. In fact, anywhere bone growth is needed because of abnormalities in bone growth or decrease in bone mass, the compositions of the present invention will find use. Examples of such therapeutic uses include, but are not limited to, 1) enhancement of periodontal treatments for the repair of damage created by periodontal disease, 2) treatments for other dental diseases, 3) enhancement of bone growth for reconstructive surgeries, 4) delay or reversal of osteoporosis 5) spinal disorders, 6) arthritis and other joint diseases and 7) augmented repair of broken bones, especially in the elderly or other with decreased regenerative abilities. Those practiced in the art will find other uses for the compositions of the present invention including the therapeutic treatment of humans and other animals.

Said exemplary uses of the compositions of the present invention may be tested using animal model systems (e.g., Cerroni A M, et al., "Effect of parity on bone mineral density in female rhesus macaques from Cayo Santiago." *Am J Phys Anthropol* July;121(3):252–69, 2003; Lane N E, et al., "Basic fibroblast growth factor forms new trabeculae that physically connect with pre-existing trabeculae, and this new bone is maintained with an anti-resorptive agent and enhanced with an anabolic agent in an osteopenic rat model." *Osteoporos Int* May 24, 2003; Yao Q, et al., "Intra-articular adenoviral-mediated gene transfer of trail induces apoptosis of arthritic rabbit synovium." *Gene Ther*

June;10(12):1055–60, 2003 and U.S. Pat. Nos. 6,410,508; 6,165,515; 5,593,833, incorporated herein by reference).

A. Screening, Diagnostics and Therapeutics

SEQ ID NO:1 and portions and mutations thereof can be used in diagnosis, prognosis, treatment, prevention, and selection and evaluation of therapies for diseases and disorders involved in bone remodeling or osteoporosis including, but not limited to, Paget's disease, osteopenia, osteoporosis, osteomalacia, rickets, including vitamin D dependent, type I and II, and x-linked hypophosphatemic rickets, Cushing's disease/syndrome, Turner syndrome, Gaucher disease, hyperparathyroidism, hypoparathyroidism, hyperthyroidism, hypogonadism, thyrotoxicosis, scurvy, calcium deficiency, systemic mastocytosis, adult hypophosphatasia, hyperadrenocorticism, osteogenesis imperfecta, homocystinuria due to cystathionine synthase deficiency, Ehlers-Danlos syndrome, Marfan's syndrome, diabetes, rheumatoid arthritis, epilepsy, primary biliary cirrhosis, chronic obstructive pulmonary disease, Menkes' syndrome, pregnancy and lactation, hepatobiliary disease, distal renal tubular acidosis, chronic renal failure, Fanconi's syndrome. and fibrogenesis imperfecta ossium.

SEQ ID NO: 1 and portions and mutations thereof may be used to screen a library of molecules for specific binding affinity. The assay can be used to screen a library of DNA molecules, RNA molecules, PNAs, peptides, ribozymes, antibodies, agonists, antagonists, immunoglobulins, inhibitors, proteins including transcription factors, enhancers, repressors, and drugs and the like which regulate the activity of the polynucleotide sequence in the biological system. The assay involves providing a library of molecules, combining the polynucleotide sequence or a fragment thereof with the library of molecules under conditions suitable to allow specific binding, and detecting specific binding to identify, at least one molecule which specifically binds SEQ ID NO:1 and portions and mutations thereof.

Similarly, SEQ ID NO:1 and portions and mutations thereof may be used to screen libraries of molecules or compounds in any of a variety of screening assays. The portion of a polypeptide employed in such screening may be free in solution, affixed to an abiotic or biotic substrate (e.g., on a cell surface), or located intracellularly. Specific binding between the polypeptide and the molecule may be measured. The assay can be used to screen a library of DNA molecules, RNA molecules, PNAs, peptides, mimetics, ribozymes, antibodies, agonists, antagonists, immunoglobulins, inhibitors, peptides, polypeptides, drugs and the like, which specifically bind the polypeptide. One method for high throughput screening using very small assay volumes and very small amounts of test compound is described in Burbaum, et al., U.S. Pat. No. 5,876,946, incorporated herein by reference, which screens large numbers of molecules for enzyme inhibition or receptor binding.

In one preferred embodiment, the polynucleotide sequences (i.e., SEQ ID NO:1 and portions and mutations thereof) are used for diagnostic purposes to determine the absence, presence, or altered-increased or decreased compared to a normal standard-expression of the gene. The polynucleotides may be at least 15 nucleotides long and consist of complementary RNA and DNA molecules, branched nucleic acids, and/or peptide nucleic acids (PNAs). In one alternative, the polynucleotides are used to detect and quantify gene expression in samples in which expression of mustang is correlated with disease. In another alternative, mustang can be used to detect genetic polymorphisms associated with a disease. These polymorphisms may be detected in the transcript cDNA.

The specificity of the probe is determined by whether it is made from a unique region, a regulatory region, or from a conserved motif. Both probe specificity and the stringency of diagnostic hybridization or amplification (maximal, high, intermediate, or low) will determine whether the probe identifies only naturally occurring, exactly complementary sequences, allelic variants, or related sequences. Probes designed to detect related sequences should preferably have at least 50% sequence identity to any of the polynucleotides encoding mustang.

Methods for producing hybridization probes include the cloning of nucleic acid sequences into vectors for the production of mRNA probes. Such vectors are known in the art, are commercially available, and may be used to synthesize RNA probes in vitro by adding RNA polymerases and labeled nucleotides. Hybridization probes may incorporate nucleotides labeled by a variety of reporter groups including, but not limited to, radionuclides such as $^{32}$p or $^{35}$S, enzymatic labels such as alkaline phosphatase coupled to the probe via avidin/biotin coupling systems, fluorescent labels, and the like. The labeled polynucleotide sequences may be used in Southern or northern analysis, dot blot, or other membrane-based technologies; in PCR technologies; and in microarrays utilizing samples from subjects to detect altered mustang expression.

Mustang can be labeled by standard methods and added to a sample from a subject under conditions for the formation and detection of hybridization complexes. After incubation the sample is washed, and the signal associated with hybrid complex formation is quantitated and compared with a standard value. Standard values are derived from any control sample, typically one that is free of the suspect disease. If the amount of signal in the subject sample is altered in comparison to the standard value, then the presence of altered levels of expression in the sample indicates the presence of the disease. Qualitative and quantitative methods for comparing the hybridization complexes formed in subject samples with previously established standards are well known in the art.

Such assays may also be used to evaluate the efficacy of a particular therapeutic treatment regimen in animal studies, in clinical trials, or to monitor the treatment of an individual subject. Once the presence of disease is established and a treatment protocol is initiated, hybridization or amplification assays can be repeated on a regular basis to determine if the level of expression in the patient begins to approximate that which is observed in a healthy subject. The results obtained from successive assays may be used to show the efficacy of treatment over a period ranging from several days to many years.

SEQ ID NO:1 and portions and mutations thereof may be used for the diagnosis of a variety of diseases or disorders associated with bone remodeling or osteoporosis. These include, but are not limited to, Paget's disease, osteopenia, osteoporosis, osteomalacia, rickets, including vitamin D dependent, type I and II, and x-linked hypophosphatemic rickets, Cushing's disease/syndrome, Turner syndrome, Gaucher disease, hyperparathyroidism, hypoparathyroidism, hyperthyroidism, hypogonadism, thyrotoxicosis, scurvy, calcium deficiency, systemic mastocytosis, adult hypophosphatasia, hyperadrenocorticism, osteogenesis imperfecta, homocystinuria due to cystathionine synthase deficiency, Ehlers-Danlos syndrome, Marfan's syndrome, diabetes, rheumatoid arthritis, epilepsy, primary biliary cirrhosis, chronic obstructive pulmonary disease, Menkes' syndrome, pregnancy and lactation, hepatobiliary disease, distal renal tubular acidosis, chronic renal failure, Fanconi's syndrome, and fibrogenesis imperfecta ossium. Examples of other uses can be found in the literature. For example, see, Nkenke, E. et al. "Bone Contact, Growth and Density Around Immediately Loaded Implants in the Mandible of Mini Pigs" *Clin Oral Implants Res* 14:312–321, 2003; Conflitti, J., et al., "Plating of Rat Fermoral Shaft Osteotomies: Report of a Technique and Preliminary Results" *Biomed Sci Instrum* 39:278–283, 2003; Pugh, D. M. and M. D. McKee, "Advances in the Management of Humeral Nonunion" *J Am Acad Orthop Surg* 11:48–59, 2003.

SEQ ID NO: 1 and portions and mutations thereof may also be used as targets in a microarray. The microarray can be used to monitor the expression patterns of large numbers of genes simultaneously and to identify splice variants, mutations, and polymorphisms. Information derived from analyses of the expression patterns may be used to determine gene function, to understand the genetic basis of a disease, to diagnose a disease, and to develop and monitor the activities of therapeutic agents used to treat a disease. Microarrays may also be used to detect genetic diversity, single nucleotide polymorphisms which may characterize a particular population, at the genome level.

In yet another embodiment, SEQ ID NO: 1 and portions and mutations thereof may be used to generate hybridization probes useful in mapping the naturally occurring genomic sequence. Fluorescent in situ hybridization (FISH) may be correlated with other physical chromosome mapping techniques and genetic map data as described in Heinz-Ulrich et al. (In: Meyers, supra, pp. 965–968).

In another embodiment, antibodies or Fabs comprising an antigen binding site that specifically binds Mustang may be used for the diagnosis of diseases characterized by the over-or-under expression of Mustang. A variety of protocols for measuring Mustang, including ELISAs, RIAs, and FACS, are well known in the art and provide a basis for diagnosing altered or abnormal levels of expression. Standard values for Mustang expression are established by combining samples taken from healthy subjects, preferably human, with antibody to Mustang under conditions for complex formation The amount of complex formation may be quantitated by various methods, preferably by photometric means. Quantities of Mustang expressed in disease samples are compared with standard values. Deviation between standard and subject values establishes the parameters for diagnosing or monitoring disease. Alternatively, one may use competitive drug screening assays in which neutralizing antibodies capable of binding Mustang specifically compete with a test compound for binding the polypeptide. Antibodies can be used to detect the presence of any peptide which shares one or more antigenic determinants with Mustang. In one aspect, the anti-Mustang antibodies of the present invention can be used for treatment or monitoring therapeutic treatment for bone remodeling disorders or osteoporosis.

In another aspect, the mustang, or its complement, may be used therapeutically for the purpose of expressing mRNA and polypeptide, or conversely to block transcription or translation of the mRNA. Expression vectors may be constructed using elements from retroviruses, adenoviruses, herpes or vaccinia viruses, or bacterial plasmids, and the like. These vectors may be used for delivery of nucleotide sequences to a particular target organ, tissue, or cell population. Methods well known to those skilled in the art can be used to construct vectors to express nucleic acid sequences or their complements. (See, e.g., Maulik et al. (1997) Molecular Biotechnology, Therapeutic Applications and Strategies, Wiley-Liss, New York N.Y.) Alternatively, mustang, or its complement, may be used for somatic cell or stem cell gene therapy. Vectors may be introduced in vivo, in vitro, and ex vivo. For ex vivo therapy, vectors are introduced into stem cells taken from the subject, and the resulting transgenic cells are clonally propagated for autologous transplant back into that same subject. Delivery of mustang by transfection, liposome injections, or polycationic amino polymers may be achieved using methods which are well known in the art. (See, e.g., Goldman, et al., (1997) Nature Biotechnology 15:462–466). Additionally, endogenous mustang expression may be inactivated using homologous recombination methods which insert an inactive gene sequence into the coding region or other targeted region of mustang (See, e.g., Thomas, et al., (1987) Cell 51: 503–512).

Vectors containing mustang can be transformed into a cell or tissue to express a missing polypeptide or to replace a nonfunctional polypeptide. Similarly a vector constructed to express the complement of mustang can be transformed into a cell to downregulate the overexpression of mustang. Complementary or antisense sequences may consist of an oligonucleotide derived from the transcription initiation site; nucleotides between about positions −10 and +10 from the ATG are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, et al., In: Huber and Carr (1994) Molecular and Immunologic Approaches, Futura Publishing Co., Mt. Kisco N.Y., pp. 163–177).

Ribozymes, enzymatic RNA molecules, may also be used to catalyze the cleavage of mRNA and decrease the levels of particular mRNAs, such as those comprising the polynucleotide sequences of the invention. (See, e.g., Rossi (1994) Current Biology 4: 469–471). Ribozymes may cleave mRNA at specific cleavage sites. Alternatively, ribozymes may cleave mRNAs at locations dictated by flanking regions that form complementary base pairs with the target mRNA. The construction and production of ribozymes is well known in the art and is described in Meyers (supra).

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiester linkages within the backbone of the molecule. Alternatively, nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases, may be included.

Further, an antagonist, or an antibody that binds specifically to Mustang may be administered to a subject to treat or prevent diseases or disorders associated with bone remodeling or osteoporosis. The antagonist, antibody, or fragment may be used directly to inhibit the activity of the polypeptide or indirectly to deliver a therapeutic agent to cells or tissues which express the Mustang. An immunoconjugate comprising a Mustang binding site of the antibody or the antagonist and a therapeutic agent may be administered to a subject in need to treat or prevent disease. The therapeutic agent may be a cytotoxic agent selected from a group including, but not limited to, abrin, ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, Pseudomonas exotoxin A and 40, radioisotopes, and glucocorticoid.

Antibodies to Mustang may be generated using methods that are well known in the art. Such antibodies may include, but are not limited to, polyclonal, monoclonal, chimeric, and single chain antibodies, Fab fragments, and fragments produced by a Fab expression library. Neutralizing antibodies, such as those which inhibit dimer formation, are especially preferred for therapeutic use. Monoclonal antibodies to Mustang may be prepared using any technique which provides for the production of antibody molecules by continuous cell lines in culture. These include, but are not limited to, the hybridoma, the human B-cell hybridoma, and the EBV-hybridoma techniques. In addition, techniques developed for the production of chimeric antibodies can be used. (See, e.g., Pound (1998) Immunochemical Protocols, Methods Mol Biol Vol. 80). Alternatively, techniques described for the production of single chain antibodies may be employed. Fabs which contain specific binding sites for Mustang may also be generated. Various immunoassays may be used to identify antibodies having the desired specificity. Numerous protocols for competitive binding or immunoradiometric assays using either polyclonal or monoclonal antibodies with established specificities are well known in the art.

Yet further, an agonist of Mustang may be administered to a subject to treat or prevent a disease associated with decreased expression, longevity or activity of Mustang.

An additional aspect of the invention relates to the administration of a pharmaceutical or sterile composition, in conjunction with a pharmaceutically acceptable carrier, for any of the therapeutic applications discussed above. Such pharmaceutical compositions may consist of Mustang or antibodies to Mustang or an epitope of Mustang, mimetics, agonists, antagonists, or inhibitors of the polypeptide. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a subject alone or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton Pa.).

For any compound, the therapeutically effective dose can be estimated initially either in cell culture assays or in animal models such as mice, rats, rabbits, dogs, or pigs. An animal model may also be used to determine the concentration range and route of administration. Such information can then be used to determine useful doses and routes for administration in humans. Exemplary amounts for administration are also listed elsewhere in this application.

A therapeutically effective dose refers to that amount of active ingredient which ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and most preferably, humans.

B. In vivo Activation of Mustang Genes

Endogenous genes can be modified in vivo through the process of homologous recombination. The techniques of homologous recombination have been used to shut off genes. When used in an organism (e.g., an animal or plant) knock-out variants of the organism can be produced. A "knock-out" is an organism that has been genetically engineered to greatly reduce or eliminate the transcription of a desired gene or genes. The production of knock-outs variant organisms is well known in the art. For example, see Olander, J and J. R. Little, "Preferential Homologous Recombinatin of H and L Chains from Mouse Myeloma Proteins Which Bind DNP Ligands" *Immunochemistry* 12:383–387, 1975; and, Scherer, S. and R. W. Davis, "Replacement of Chromosome Segments with Altered DNA Sequences Constructed in vitro" *Proc Natl Acad Sci, USA* 76:4951–4955, 1979.

The techniques of homologous recombination can also be used to "turn on" desired genes in a cell, tissue, organ or organism. In these techniques, a promoter sequence is introduced into a gene or gene promoter region. The introduced promoter sequence may be a promoter that turns on the gene constitutively or it may be an inducible promoter. An inducible promoter can be "turned on" or induced to activate gene transcription by supplying the inducing agent(s) to the transfected cell or organism. The metallothione promoter is an example of an inducable promoter. Examples of techniques useful for the homologous recombination of genes in vivo to activate a desired gene are given in U.S. Pat. Nos. 6,270,989; 6,303,379 and 6,355,241, which are incorporaated herein by reference. Likewise, the techniques of homologous recombination for these purposes have been well known in the art for twenty plus years. For example, see Gattoni, S., et al., "Relationship Between Integrated and Nonintegrated Viral DNA in Rat Cells Transformed by Polyoma Virus" *J Virol* 34:615–626, 1980; and, Poteete, A. R. and M. R. Volkert, "Activation of recF-dependent Recombinatin in *Escherichia coli* by Bacteriophage lambda- and P22-encoded Functions" *J Bacteriol* 170:4379–4381, 1988.

Experimental

The following examples serve to illustrate certain preferred embodiments and aspects of the present invention and are not to be construed as limiting the scope thereof.

In the disclosure which follows, the following abbreviations apply: ° C. (degrees Centigrade); g (gravitational field); vol (volume); w/v (weight to volume); v/v (volume to volume); BSA (bovine serum albumin); CTAB (cetyltrimethylammonium bromide); fmol (femtomole); FPLC (fast protein liquid chromatography); HEPES (N-[2-Hydroxyethyl]-piperazine-N-[2'-ethanesulfonic acid]); HPLC (high pressure liquid chromatography); DTT (dithiothreitol); DMF (N,N dimethyl formamide); DNA (deoxyribonucleic acid); i.d. (internal diameter); p (plasmid); µl (microliters); ml (milliliters); µg (micrograms); pmoles (picomoles); mg (milligrams); MOPS (3-[N-Morpholino]propanesulfonic acid); M (molar); mM (milliMolar); µM (microMolar); nm (nanometers); kdal (kilodaltons); OD (optical density);

EDTA (ethylene diamine tetra-acetic acid); FITC (fluorescein isothiocyanate); LC sulfo SPDP (LC sulfo-N-succinimidyl-3-(2-pyridyldithio)proprionate); SDS (sodium dodecyl sulfate); NaPO$_4$ (sodium phosphate); Tris (tris (hydroxymethyl)-aminomethane); PMSF (phenylmethylsulfonylfluoride); TBE (Tris-Borate-EDTA, e.g., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); Tween (polyoxyethylene-sorbitan); Boehringer Mannheim or BM (Boehringer Mannheim, Indianapolis, Ind.); New England Biolabs or NEB (New England Biolabs, Beverly, Mass.); Novagen (Novagen, Inc., Madison, Wis.); Pharmacia (Pharmacia Biotech Inc., Piscataway, N.J.); Perkin Elmer (Perkin Elmer, Norwalk, Conn.); Pierce (Pierce Chemical Co., Rockford, Ill.); Promega (Promega Corp., Madison, Wis.); Qiagen (Qiagen Inc., Chatsworth, Calif.); Stratagene (Stratagene Cloning Systems, La Jolla, Calif.); USB or U.S. Biochemical (U.S. Biochemical, Cleveland, Ohio).

EXAMPLE 1

Transcriptional Activity in the Fracture Callus. To establish an in depth understanding of the transcriptional activity occurring during the early stages of a healing rat femur fracture, RNA was examined from four different time points (post-fracture [PF] days 3, 5, 7, and 10) and compared with that of intact bone (containing cartilage and bone marrow). Briefly, the fracture model is performed as follows: All methods and animal procedures were reviewed and approved by the University's Laboratory Animal Users Committee and met or exceeded all federal guidelines for the humane use of animals in research. The rat femur fracture model was described previously (Bonnarens, F. & Einhorn, T. A., J. Orthop. Res. 2:97–101, 1984) and used extensively in our studies (Hadjiargyrou, M., et al., J. Bone Miner. Res. 15:1014–1023, 2000; Hadjiargyrou, M., et al., Bone (NY) 9:149–154, 2001; Hadjiargyrou, M., et al., Biochem. Biophys. Res. Com. 249:879–884, 1998). A set of four animals was euthanized each at 3, 5, 7, 10, and 14 days post-fracture (PF) and a set of three animals at 21 days. Following euthanasia by CO$_2$ inhalation, the contralateral control femur from each animal, as well as the fracture calluses, were dissected free and processed for RNA extraction.

The initial time points were selected to represent specific physiological events of the healing callus, including inflammation, chondrogenesis, and ossification (FIG. 2). The spatial complexity and structural interdependence of these early events of the mammalian callus have been described previously (Jingushi, S., et al., J. Bone Miner. Res. 7:1045–1055, 1992; Sandberg, M. M., et al., Clin. Orthop. Rel. Res. 289:292–312, 1993; Einhorn, T. A., Clin. Orthop. 355, S7–21, 1998; Hadjiargyrou, M., et al., J. Bone Miner. Res. 15:1014–1023, 2000; Hadjiargyrou, M., et al., Bone (NY) 9:149–154, 2001). Of the 4,500 cDNAs derived from suppressive subtractive hybridization (SSH), 3,635 were successfully sequenced (contained a readable insert). Briefly, SSH was performed as follows: The samples used for these analyses were derived by pooling the RNA (see below) from two intact femurs and comparing it with RNA pooled from the fracture callus tissues of one animal harvested at each of PF days 3, 5, 7, and 10. Complimentary DNAs were synthesized from 1 ug total RNA using the SMART PCR cDNA synthesis kit (CLONTECH), and subtractive hybridization was performed with a PCR-select cDNA subtraction kit (CLONTECH). cDNAs derived from the fracture callus material, considered the "tester" pool, and cDNAs from intact femurs, considered the "driver" pool, were digested in RsaI (New England Biolabs). To select transcripts up-regulated by the fracture repair process, PCR adaptors were ligated to the tester pool population (fracture callus). The tester cDNA pool was then hybridized with excess cDNAs (15-fold) from the driver pool (control bones). After hybridization, suppression PCR using primers specific for the tester PCR adaptors selectively amplified differentially expressed transcripts. Amplified cDNA sequences were then ligated into the T/A cloning vector pT-Adv (CLONTECH). Approximately, 4,500 cDNA clones were sequenced using an ABI 3700 DNA sequencer (Applied Biosystems). Finally, all sequences were checked for homology using the BLAST algorithm found at www.ncbi.nlm.nih.gov/blast/. For blastn, ~65% of the sequences had E values of $2.0 \times 10^{-19}$ or better (parameters: BLOSUM62; word size 12). For blastp, ~40% of the sequences had E values of $1.0 \times 10^{-6}$ or better (parameters: BLOSUM62; default NCBI Gap Costs).

Briefly, RNA purification was performed as follows: Total RNA was isolated from each individual fracture callus, as well as from each intact bone, which included bone marrow and articular and normal growth plate cartilage, using the ToTALLY RNA kit (Ambion) based on the method of Chomczynski and Sacchi (Chomczynski, P. & Sacchi, N., Anal. Biochem. 162:156–159, 1997) and as described previously (Hadjiargyrou, M., et al., J. Bone Miner. Res. 15:1014–1023, 2000; Hadjiargyrou, M., et al., Bone (NY) 9:149–154, 2001; Hadjiargyrou, M., et al., Biochem. Biophys. Res. Com. 249:879–884, 1998).

After BLAST searches, of 3,635 clones, 65.8 percent had homology to 588 known genes (represented as 382 singletons), 31 percent had homology to 821 ESTs, and the remaining 3.2 percent (116) had no homology match and presumably represent completely novel genes. The known genes reflected a variety of families with diverse functions in cell cycle regulation, cell matrix and cell adhesion, ECM construction, inflammation, general metabolism, signaling, transcriptional regulation, protein transport, etc. (Table 1). The abundance of each gene within the library (represented as # of clones) is also indicated in this table. Several genes encoding for matrix proteins like collagens, osteopontin, osteonectin, fibronectin (Jingushi, S., et al., J. Bone Miner. Res. 7:1045–1055, 1992; Sandberg, M. M., et al., Clin. Orthop. Rel. Res. 289:292–312, 1993; Hirakawa, K., et al., J. Bone Miner. Res. 9:1551–1557, 1994; Hiltunen, A., et al., FEBS Lett. 364:171–174, 1995; Yamazaki, M., et al., J. Orthop. Res. 15:757–764, 1997), and growth factors FGF, IGF, TGF (Barnes, G. L., et al., J. Bone Miner. Res. 14:1805–1815, 1999), already known to be highly upregulated during the fracture repair process, were present and were interpreted to be indicative of the success of SSH. In addition, the most abundant genes present were also matrix genes such as collagen type I (½, 240 clones), collagen type III (190 clones), OSF-2 (95 clones), tenascin (59 clones), and fibronectin (57 clones) (Table 1).

EXAMPLE 2

Temporal Gene Expression Analysis via Custom-made cDNA Arrays. Given the large number of cDNA clones present in the subtracted library, it was deemed practical to analyze the expression of all cDNA clones simultaneously through the use of custom microarrays. These microarrays included the complete subtracted library (3,635 cDNAs), as well as 257 control spots. Briefly, differential screening of the fracture callus-induced transcript library was performed through a series of steps. First, individual colonies were grown overnight at 37° C. in 500 ml of Luria broth medium containing 50 g/ml ampicillin. The next morning, 2 ml of the culture was transferred to individual wells of a 96-well PCR plate containing 98 ml of PCR master mix (10 ml of 10× PCR buffer, 2 ml of 10 mM pT-Adv nested primers 1 and 2, 1 ml of 20 mM dNTPs, 82 ml of sterile $H_2O$, and 1 ml of Taq DNA polymerase (PerkinElmer Life Sciences). Using the GeneAmp PCR System 9600 (PerkinElmer Life Sciences), PCR amplification was performed by cycling for 2 min at 94° C. followed by 35 cycles consisting of 40 s at 95° C. and 3 min at 68° C. PCR amplification products were analyzed by electrophoresis on a 1% agarose gel, and 90% of the clones were found to contain inserts, with an average insert size of 250–500 bp.

To prepare nylon arrays of the PCR-positive clones, free primers were removed from the PCR reactions by filtration and the samples concentrated to ~50 ng/ml. Each sample was then spotted on the nylon filters (0.25 l/spot). In addition to the 3,635 subtracted cDNA clones (representing all 588 known genes, the 821 ESTs and 116 novel sequences), 257 control samples were also spotted (mitochondrial DNA, ribosomal RNA, genomic DNA, plasmid, actin, tubulin, GAPDH, yeast DNA, buffer, bacterial DNA (*Escherichia coli/Bacillus subtilis*), as well as mammalian DNA (mouse, rat, human, monkey)). Membranes were denatured by soaking for 10 min in a solution of 0.5 mM NaOH, 1.5 mM NaCl, and neutralized by successive 5 min washes in 0.5 mM Tris-HCl (pH 8.0), 1.5 mM NaCl, and 2× sodium chloride-sodium citrate (SSC) buffer. The membranes were then UV cross-linked using a Stratalinker (Stratagene).

Initially, experiments utilizing the identical RNA samples (from single animal per time point) used in SSH were utilized to confirm the hybridization results, as well as the production and integrity of the microarrays. Results from these experiments yielded reproducible data between each run (data not shown). Once confirmed, RNA samples from multiple animals at each specific PF time point were pooled (n=3), and hybridizations of arrays were repeated to show how transcriptional activity was modulated as a function of time in the healing process as compared with RNA samples from intact bone (n=3). Briefly, RNA derived from the calluses of three animals was pooled for each separate time point (PF days 3, 5, 7, 10, 14, and 21). The RNA sample representing intact bone was established by pooling specimens from intact femurs of three different animals. The protocol used for labeling target, hybridization, and washings was identical to that for GeneFilters from Research Genetics, with the exception that the last wash was carried out in a stringent wash in 0.2×SSC, 0.1% SDS at 65° C. for 30 min. Subsequently, all the blots were simultaneously exposed to a PhosphorImager screen (Amersham Biosciences) for 3 days prior to capturing the final image using a PhosphorImager (Amersham Biosciences). Each membrane image was analyzed using the GenePix Pro (version 3.0) microarray software package. Measurements of the optical intensity of the 244 pixels contained within each spot generated a median intensity value. The average background intensity was then calculated from the 1,060 blank spots scattered throughout each membrane. This average background intensity was then subtracted from the median intensity of each spot and normalized to the 18 S ribosomal RNA-positive control spots. Finally, replicate spots for each gene were averaged prior to further analysis.

Hybridization was performed using a total of seven identical membranes, one for each of the six PF time points (days 3, 5, 7, 10, 14, and 21), as well as one for intact bone (control). We found that 90 percent and 80 percent of the subtracted known genes and ESTs are up-regulated ( 2.5-fold) during the repair process (at any given PF day), respectively. The remaining cDNA clones probably represent false positives, most likely resulting from the SSH. Representative membranes following hybridization of RNA isolated from intact bone and PF day 10 callus are shown in FIG. 3 and clearly demonstrate differential gene expression.

Figure 4:
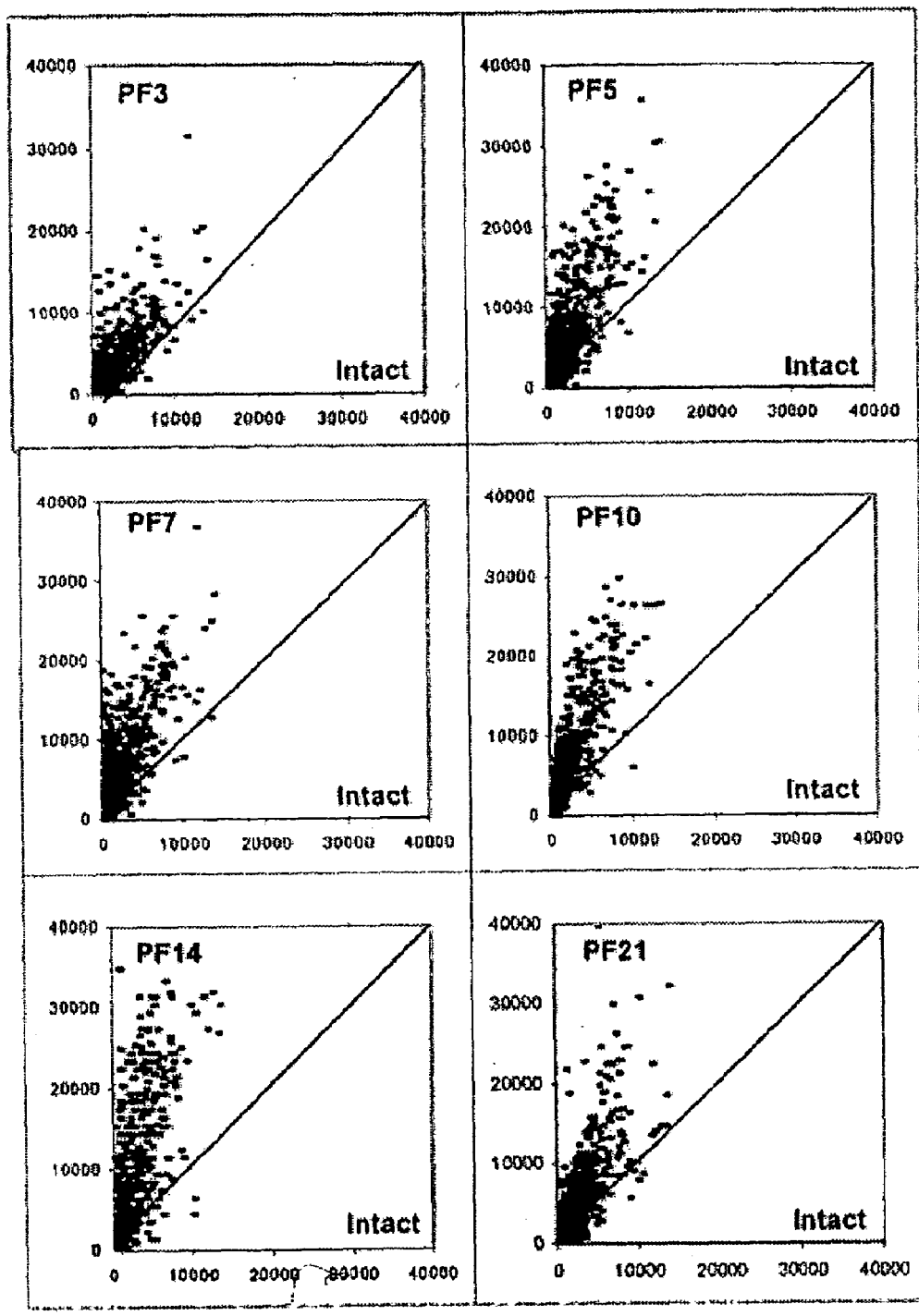
FIG. 4 shows temporal gene expression profiles derived from microarrays. In each graph, the hybridization signal intensity of each spot is plotted on the y axis for PF day and on the x axis for intact. The diagonal line indicates a ratio of one or no change in expression. For genes represented by multiple cDNAs, the average was determined and is represented by a single dot.

Data resulting from imaging the seven filters was used to generate scatter plots, representing the ratio for each gene between each of the PF day callus (y axis) over that of intact bone (x axis, FIG. 4). The figure clearly shows the increased gene expression (shift of dots to the y axis) during the progression of the fracture callus through its early stages (PF days 3–10), thus confirming the initial subtraction (designed to identify upregulated genes). Relative to intact bone, the highest level of expression is observed at PF day 14 (note the higher intensity and shift of dots), and by PF day 21, expression levels begin to decline toward the control (represented by diagonal line, FIG. 4). Based on these data, the exact temporal expression levels of all known genes are shown in Table 2 and demonstrate that the expression patterns change extensively throughout the healing process and that these shifts are distinctly different from gene to gene. Finally, the fold change in expression observed in this study for many of these genes (i.e., collagens, osteopontin, osteonectin, etc.) are consistent with those previously determined using Northern analyses by our laboratory (Hadjiargyrou, M., Ahrens. W. & Rubin, C. T. (2000) *J. Bone Miner. Res.* 15, 1014–1023; Hadjiargyrou, M., Rightmire, E. P., Ando, T. & Lombardo, F. T. (2001) *Bone* (N. Y.) 9, 149–154), as well as others (Sandberg, M. M., et al., *J. Bone Miner. Res.* 9, 1551–1557, 1994; Hiltunen, A., et al., *FEBS Lett.* 364:171–174, 1995; Sakano, S., et al., *J. Bone Miner. Res.* 14:1891–1901, 1999).

EXAMPLE 3

Clustering Analysis of ESTs and Novel cDNAs. In an attempt to group known genes, ESTs and novel cDNAs based on their co-regulated expression patterns, cluster analysis was performed using data derived from the microarray experiments. Briefly, clustering of the up-regulated genes, as a function of time, was performed using average linkage analysis following data normalization and filtering (includes background subtraction and normalization as stated above (Image analysis)). In addition, a block effect correction was also performed. We defined blocks in two directions. First, 38 rank blocks were generated based on the mean intensity value for each gene, and second, four (2×2) adjacent blocks were combined. Each of these block effects was calculated using a generalized linear model and corrected from the intensity which led to the residual value from the generalized linear model fitting. Finally, the median of each rank block for each array was added to this residual. Since a single representative value was needed for each gene, and since some genes were represented by multiple cDNA clones (more than one spot on the membrane), some spots that generated inconsistent expression patterns as compared with others (of the same gene) were considered as outliers and were filtered out. Based on correlation (both Pearson's and Spearman's), 403 spots were excluded due to their inconsistent expression patterns (as described previously), and another 29 spots were excluded because of their low expression level (negative intensity values). With this normalized intensity value, we performed pairwise average linkage cluster analysis to establish clusters by grouping genes which shared the same/similar temporal expression patterns. Pearson's correlation coefficient, which statistically captures similarity in "shape" was used as similarity measure. The final number of clusters was determined to be 16 using pseudo F and pseudo $t^2$ statistics (Calinski, T. & Harabasz, J. (1974) Commun. Stat. 3, 1–27; Duda, R. O. & Hart, P. E. (1973) Pattern Classification and Scene Analysis, John Wiley & Sons, Inc., New York). To show that the final selection and number of clusters were reasonable, intracluster correlations of each of the 16 clusters, as well as the results from discriminant analysis, were examined. This data analysis was performed in logarithm base 2 space after standardization.

Figure 5:
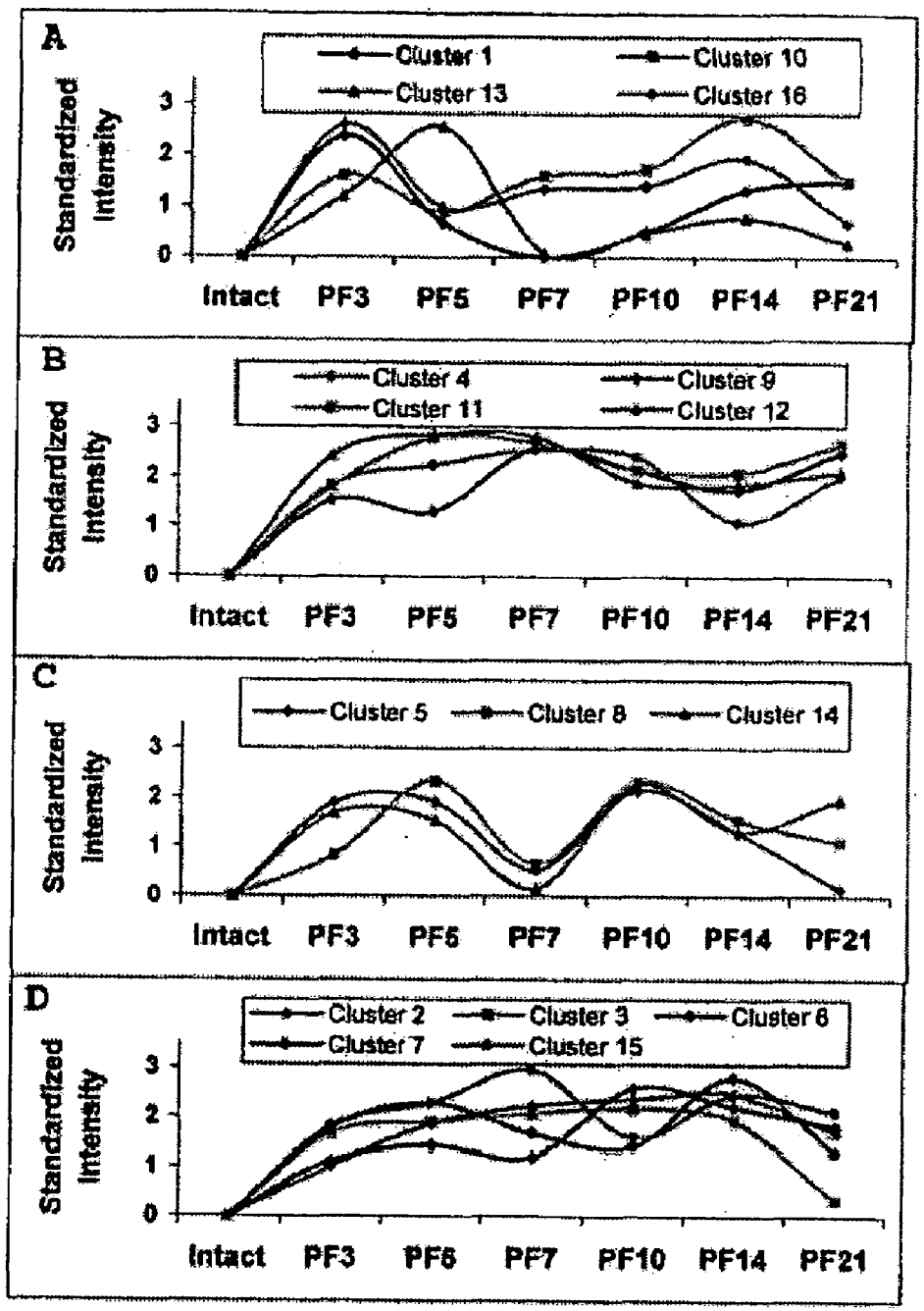
FIG. 5 shows cluster analysis of microarray data. Hierarchical clustering was used to group the identified genes based on similar expression patterns over the seven time points examined (Intact and PF3, PF5, PF7, PF10, PF14, and PF21). Although 16 clusters were initially identified, 4 graphs are shown with multiple clusters that display a similar time-dependent expression pattern. A, Clusters 1, 10, 13, and 16. B, Clusters 4, 9, 11, and 12. C, Clusters 5, 8, and 14. D, Clusters 2, 3, 6, 7, and 15.

Statistical analysis generated 16 distinct clusters (FIG. 5 and Table 3). A common feature of each cluster is the trend of the expression pattern, which invariably shifts upwards from intact to PF, indicating the expected upregulated expression of genes relative to intact bone. Furthermore, the clusters show distinct patterns of expression, ranging from gene activity which peaked early and then declined (FIG. 5A, Clusters 1, 10, 13, and 16), to clusters that continue to rise through the healing process (FIG. 5B, Clusters 4, 9, 11, and 12). A number of other clusters show a pattern of successive increased and decreased expression, indicating fluctuations in general metabolic activity (FIG. 5C, Clusters 5, 8, and 14). A final group of clusters display a pattern of a steady increase for the first 2 weeks and then a sharp decline by the 3rd week (FIG. 5D, Clusters 2, 3, 6, 7, and 15), indicating the end of various physiological processes (FIG. 2).

Clusters 2 and 3 contained the greatest number of genes that included the majority 5 of the well known matrix genes (e.g., collagen types I, II, III, IV, V, VI, XI, and XII and bone sialo-protein, osteonectin, osteopontin, fibronectin, laminin, lumican, versican, tenascin, decorin, biglycan, and glypican), growth factors (IGF-I, TGF-, FGF-7), growth factor receptors (PDGF and NGF), transcription factors (hypoxia inducible factor 1, c-fos, and Sox9), as well as a very large number of genes representing other gene families (Table 3). In addition, these two clusters also included over 600 functionally unknown genes (57%) represented either as novel or EST sequences or known genes with no assigned function.

EXAMPLE 4

Figure 6:
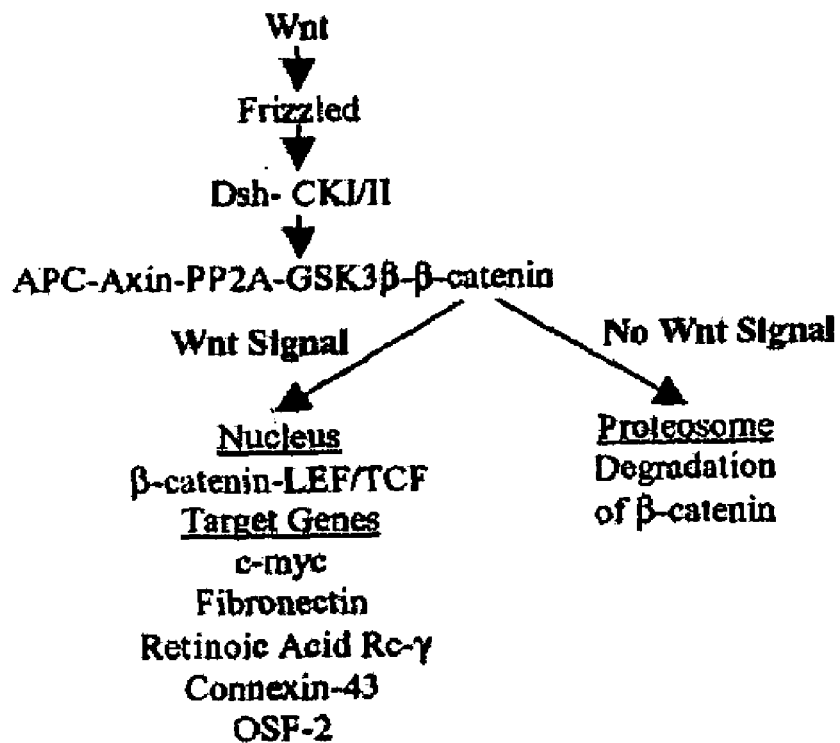
FIG. 6 shows a model of Wnt Signaling. Binding of the secreted growth factor Wnt to the cell-surface receptor Frizzled activates Dishevelled (Dsh). The exact mechanisms of signal transduction from Frizzled to Dsh and subsequently to glycogen synthase kinase 3b (GSK3) remain unknown. Casein kinases I and II (CKI/II), positive regulators, act downstream of Dsh and regulate the b-catenin pathway. Increased cytoplasmic b-catenin forms complexes with the LEF/TCF family of transcription factors and activates expression of target genes. The absence of a Wnt signal leads to the formation of a b-catenin complex with axin, the tumor suppressor APC, phosphatase A2 (PP2A), and glycogen synthase kinase 3b. b-Catenin is subsequently phosphorylated by glycogen synthase kinase 3b, and this leads to its degradation by the ubiquitin-proteosome pathway.

Identification of the Wnt Signaling Pathway. Since there were many signaling molecules present in our subtracted cDNA library (Table 1), we decided to examine the possibility of identifying active pathways that participate in bone regeneration. One of the more complete signaling pathways identified (based on the number of involved molecules) is the Wnt signaling pathway (Huelsken, J. & Birchmeier, W. (2001) Curr. Opin. Genet. Dev. 11, 547–553) (FIG. 6). More specifically, we identified Wnt-5A, Frizzled, casein kinase II, b-catenin, and phosphatase 2A, all of which were robustly up-regulated during the repair process (Table 4). In addition, we also show the identity and expression levels of a number of genes that represent known transcriptional targets of the Wnt pathway (i.e., c-myc, fibronectin, retinoic acid receptor gamma, connexin 43, and OSF-2) (Table 4).

EXAMPLE 5 cDNA Microarray Analysis. Above, we showed the transcriptional complexity of bone regeneration as determined by SSH and custom microarrays (Hadjiargyrou M, et al., Transcriptional profiling of bone regeneration: Insight into the Molecular Complexity of Wound Repair. J Biol Chem 277:30177–30182, 2002) A large number (821) of ESTs were identified as upregulated during the early stages of fracture repair (PF day 3–10). From this pool of ESTs, we initially focused on several that appeared as multiple cDNAs and with demonstrated high levels of expression (>2.5 fold over intact). For example one such EST (Accession #AA943790) was represented by eight different cDNA clones with average levels of expression (as determined by microarray analysis) that were 3.1, 4.9, 6.8, 5.7, 5.0, 4.4 fold higher than intact at PF day 3, 5, 7, 10, 14, and 21, respectively. The actual microarray filters derived from hybridization to intact and PF day 5 RNAs and showing one of the eight clones representing EST AA943790 clearly demonstrate the change in expression (FIG. 7, arrow). Another spot representing Collagen Type I is shown as a comparison (FIG. 7, arrowhead). In addition, FIG. 7 shows that the expression of some other genes did not change (small arrows).

EXAMPLE 6

Full Length Cloning and Sequence Analysis. Initially, we designed primers based on the original AA943790 EST sequence and subcloned the expected 581 bp cDNA fragment. Following verification by DNA sequencing, we performed northern blot analysis (data not shown) to confirm that this gene was in fact expressed in the callus and displayed differential expression (Garman R, Lombardo F, Hadjiargyrou M 2001 Identification of a novel fracture repair-specific gene expressed during early callus formation Ann Biomed Eng 29:S-89 (Abstract)). Northern blot analysis was performed as follows: Total RNA (15–20 mg) from multiple samples was prepared, fractionated on a 1% formaldehyde/agarose gel, transferred to a nylon membrane (Nytran), and ultraviolet cross-linked according to standard procedures. cDNA probes were random primer-labeled with 32P-dCTP and hybridized to the membrane at 65° C. overnight in a solution containing 15% formamide, 200 mmol/L $NaPO_4$ (pH 7.2), 1 mmol/L ethylene-diamine tetraacetic acid (EDTA), 7% sodium dodecylsulfate (SDS), and 1% bovine serum albumin (BSA). Following hybridization, the blot was washed in a solution of 2×SSC/1% SDS at 50° C. for 30 min, 0.2×SSC/1% SDS at 50° C. for 30 min, and 0.2×SSC/0.1% SDS at 65° C. for 30 min. For quantitative measurement of relative expression level of MUSTANG, the amount of bound probe was measured by exposing the labeled filter to a Kodak phosphoimager screen. The image was then captured using a phosphoimager (Molecular Dynamics) and the signal intensity was then measured using Image Quant software package (version 4.0). The intensity level obtained of the MUSTANG probe, after subtracting background, was then normalized to the GAPDH signal of the same filter. The values plotted represent fold change compared to intact bone after background subtraction and GAPDH normalization. Following each experiment, the membrane was stripped of probe by immersion in boiling water for 30–60 sec and then used for hybridization. Thus, the same RNA membrane was used in the hybridization of both cDNA probes. Tissue blots were prepared in a similar fashion and probed with the MUSTANG cDNA.

Once verified, we then decided to clone the full-length cDNA using a bioinformatics approach, forming a "contig" (a series of overlapping homologous ESTs). Using the original AA943790 nucleotide sequence (581 bp) a contig was generated based on BLAST algorithm (http://www.ncbi.nlm.nih.gov/BLAST/) searches that resulted in a 1220 bp DNA fragment (two other ESTs were used to extend the original, one at the 5' end and the other at the 3' end). Our contig criteria were very stringent, with at least a 100 bp stretch of nucleotides with >93% homology. Next, a set of specific RT-PCR primers were designed based on this contig sequence in order to experimentally obtain a smaller 1025 bp fragment containing a putative 246 bp open reading frame (ORF), as well as 5' and 3' untranslated region (UTR) sequences (includes 3' polyadenylation site). RT-PCR was performed using the Qiagen RT-PCR kit according to the manufacturer's protocol (Qiagen). Primers were designed based on contig sequence and predicted open reading frame (see, FIG. 1). A 50 ml reaction was set up using the following PCR conditions: 50° C. for 30 min, 94° C. for 10 min, and 40 cycles of 94° C. for 30 sec, 65° C. for 1 min, and 72° C. for 1 min. The PCR products were analyzed on a 1% agarose gel. Subcloning was accomplished using the PCR-Trap Cloning kit (Gene Hunter). The cloned cDNA was then confirmed by DNA sequencing.

RT-PCR was subsequently performed using PF day 5 callus RNA as a template and the expected 1025 bp fragment was obtained, subcloned, and sequenced. The exact nucleotide sequence of this 1025 bp fragment confirmed the one generated by the contig approach and is shown in FIG. 1A. This 1025 bp full length cDNA clone contains the predicted 246 bp ORF encoding a small protein of 82 amino acids (aa) with a calculated molecular weight (MW) of ~9,6 kDa. (FIG. 1A).

Once we were able to verify the ORF, we then used the predicted aa sequence to search Genbank for homologous proteins. None of our BLAST searches resulted in any known homologous proteins, with the exception of a mouse hypothetical protein originally isolated from skeletal muscle (Accession #AJ277212). Interestingly, using translated BLAST searches (tblastn) of EST databases, we were able to identify homologous EST aa sequences from other species, including, human, mouse and cow. The homology between our rat MUSTANG aa sequence and that of these other species is shown in FIG. 1B. The actual level of aa homology between rat and mouse, human, and bovine is 93%, 88% and 85%, respectively. Further, the majority of aa changes detected between rat MUSTANG and its homologues are represented by conservative substitutions. For example, even though there are five aa substitutions between rat MUSTANG and its mouse homologue, four of them (S/T, S/A, E/D, and I/V) are conservative (FIG. 1B).

The MUSTANG aa sequence also revealed a classic nuclear import signal (PIKKKRPPV, aa 10–18 [SEQ ID NO: 3]), indicating that it is a nuclear protein (FIG. 1B). In fact, using the PSORT II algorithm (http://psort.nibb.acjp), it was predicted that rat MUSTANG is a nuclear protein with a 94.1% reliability score. Finally, no other specific motif was detected, with the exception of an N-myristoylation, N-glycosylation, and Casein kinase II phosphorylation sites. Lastly, the classic polyadenylation site, AATAAA (SEQ ID NO: 4) is also present at the 3' end UTR (FIG. 1A).

EXAMPLE 7

In vitro Transcription Translation/Fusion Protein. To determine whether the full length MUSTANG cDNA encoded for the predicted 82 aa protein described above, we used an in vitro transcription/translation assay (TNT T7 Quick Coupled Transcription/Translation System, Promega). Using the subcloned MUSTANG cDNA (from fracture callus) in both, correct (5'-3') and reverse (3'-5') orientation, in relation to the T7 promoter, we were able to obtain the expected protein product derived from the MUSTANG clone only in the correct orientation (data not shown). This protein had an approximate size of 9–10 kDa, which corresponds to the molecular weight (9.6 kDa) estimated from the predicted aa sequence. To verify that this is indeed a nuclear protein, a gene fusion protein was created by the insertion of the MUSTANG cDNA into a GFP vector.

In order to assess MUSTANG protein localization, an GFP-MUSTANG fusion protein was constructed. Primers containing unique 5' EcoRI and 3' BamHI restriction sites were designed and used to amplify the complete MUSTANG coding region. Agarose gel electrophoresis was used to confirm the presence of the expected 282 base pair product, which was then excised from the gel and purified (MinElute, Qiagen, Inc). The fragment was then restriction digested and ligated into the pECFP-C1 Vector (Clonetech laboratories, Inc.), which is under the control of the CMV promoter and leads to the generation of a fusion protein with MUSTANG fused to the carboxyl terminus of GFP. Potential GFP-MUSTANG plasmids were isolated from transformed cells (Plasmid Mini-Prep, Qiagen, Inc.) and screened for the presence of the MUSTANG cDNA insert by PCR. The correct (5'-3') orientation and frame of the MUSTANG insert were then verified by sequencing. Bacterial stocks containing the verified GFP-MUSTANG plasmid were used for the isolation of GFP-MUSTANG plasmid DNA for the subsequent transfection experiments.

Transient transfections with the GFP-MUSTANG construct and parental pECFP-C1 plasmids were carried out to determine the intracellular localization of MUSTANG within pre-osteoblastic MC3T3 cells. Transient transfection studies were performed using MC3T3-E1 pre-osteoblastic cells that were maintained in log growth phase using a-MEM supplemented with 10% FBS (Life Technologies, Grand Island, NY). Cells were plated in standard 6-well tissue culture plates containing glass cover slips at an initial density of $1 \times 10^5$ cells/well and transfected with GFP-MUSTANG plasmid, facilitated by the addition of the transfection reagent FuGene 6 (Roche) at a 9:2 ratio (ml fugene: mg DNA). As a negative control, transfections were carried out in the same manner using the parental pECFP-C1 vector. After 48 hours, the cells were washed, fixed in 4% paraformaldehyde, mounted and imaged with phase contrast and epi-fluorescence confocal microscopy at the University Microscopy Imaging Center (University Hospital and Medical Center, SUNY Stony Brook).

Figure 8:
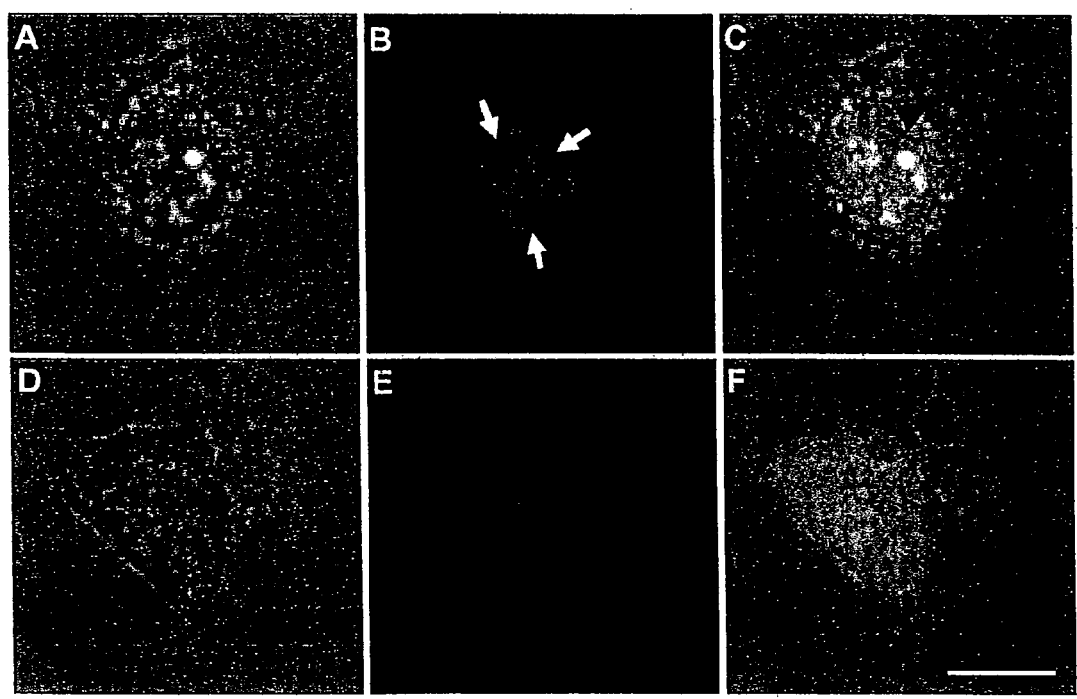
FIG. 8 shows the nuclear localization of mustang fusion protein. Pre-osteoblastic MC3T3 cells were transiently transfected with the GFP-mustang plasmid encoding an enhanced green fluorescent protein-mustang fusion and the parental pECFP-C1 vector. All images were obtained under phase contrast and epi-fluorescence confocal microscopy at 600× magnification. A and D. Phase contrast images of cells transfected with GFP-MUSTANG and pECFP-C1, respectively. B and C. Seen under epi-fluorescence, GFP-.MUSTANG localizes in the nucleus, but not in nucleoli (arrows) or nuclear envelope (arrowheads). E. The vector GFP is evenly dispersed throughout the cell. C and F. Overlaid images of the phase and fluorescence images clarify the nuclear localization of GFP-MUSTANG compared to the broad dispersal of GFP. Scale bar is equal to 50 μm.

The nuclei of cells transfected with GFP-MUSTANG labeled brightly, with virtually no fluorescence seen in the cytoplasm, indicating active translation and nuclear import of the GFP-MUSTANG fusion protein (FIGS. 8A–C). In contrast, the nucleoli, sites of rRNA synthesis, as well as the nuclear envelope were devoid of any staining (FIG. 3B arrows and 3C arrowheads, respectively). Transfection with the parental vector resulted in diffuse labeling throughout the cells, demonstrating active GFP translation with no apparent sub-cellular localization (FIGS. 8D–F). From these results it is clear that the MUSTANG nuclear import signal identified through the aa analysis is present in the final protein product and directs MUSTANG to the nucleus.

EXAMPLE 8

Figure 9:
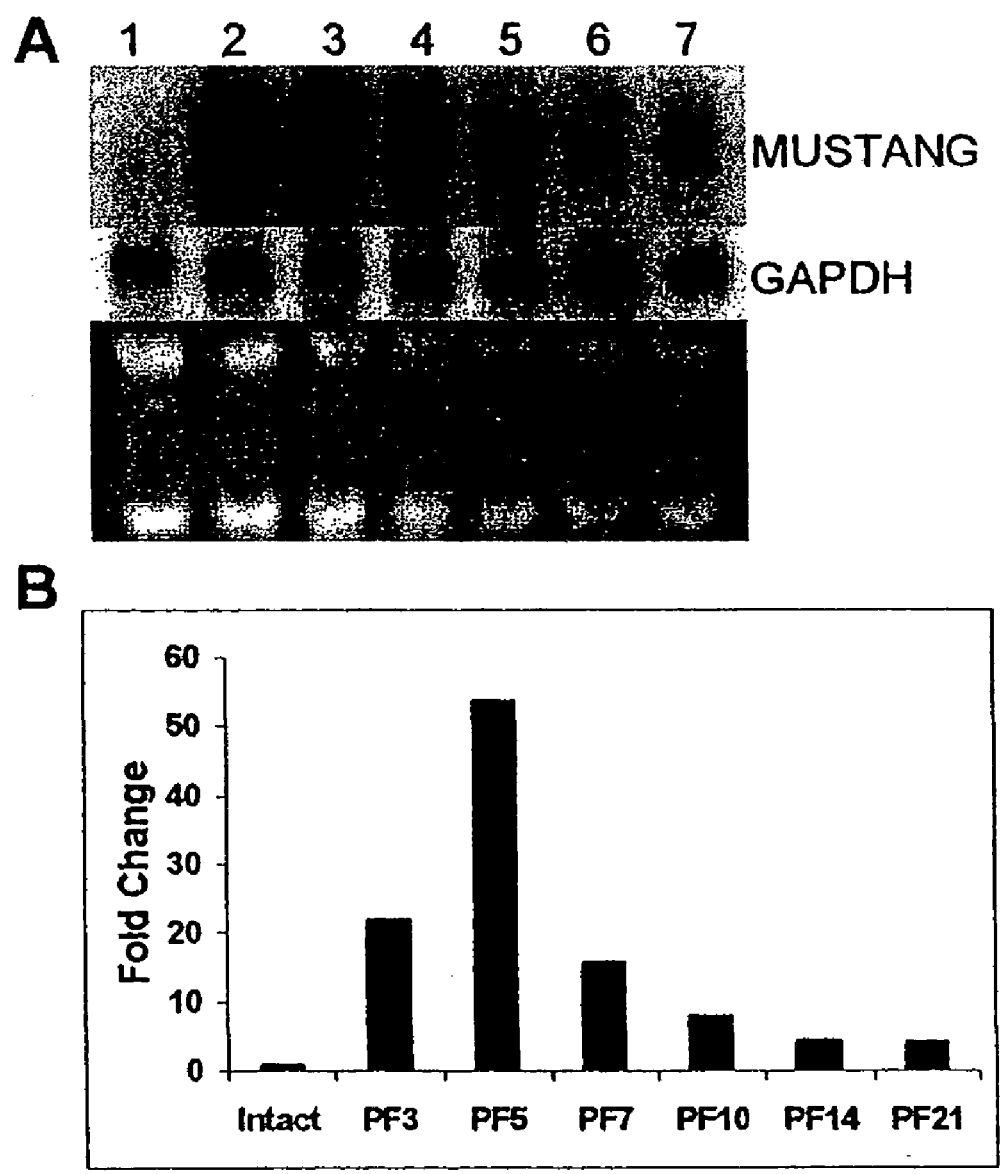
FIG. 9 shows the temporal expression of mustang mRNA during fracture repair. A. Total RNA from an intact femur (contains bone marrow, articular and normal growth plate cartilage, lane 1) and different PF day calluses (3, 5, 7, 10, 14, 21, lanes 2-7, respectively) was analyzed by northern blotting using random labeled probes (mustang, Top Panel and GAPDH, Middle Panel). The RNA membrane used in this experiment is shown below indicating the integrity and amounts of RNA loaded per lane (Bottom Panel). B. Graph indicating the fold change in mustang mRNA expression compared to intact bone (based on phosphoimager intensity measurements of bands shown in A and normalized to GAPDH)

Temporal Expression of MUSTANG mRNA. To confirm the cDNA microarray studies and to more accurately determine changes in expression between intact bone and fracture calluses, we prepared nylon membranes with RNA isolated from intact bone (contains bone marrow, articular and normal growth plate cartilage) and PF day 3, 5, 7, 10, 14, and 21 callus. FIG. 9 confirms our previous results and clearly shows that the 1.2 kb MUSTANG mRNA transcript is almost absent from intact bone but in contrast is acutely up-regulated during PF day 3 and 5. It then gradually declines by PF day 7 and 10 and further decreases to very low, though still higher than intact bone levels by PF day 14 and 21 (FIG. 9).

The relative levels of MUSTANG mRNA during the maturation of the fracture callus were accurately determined by integrated optical density measurements (normalized to those of GAPDH mRNA) and are shown in FIG. 9B. When compared to intact bone, MUSTANG mRNA expression in the callus dramatically rises to an approximate 22 fold increase by PF day 3, a staggering 54 fold by PF day 5 and then declines to lower levels, of 16, 8, 4.5 and 4.2 fold by PF day 7, 10, 14 and 21, respectively (FIG. 9B). Even at the lowest mRNA levels (PF day 21), MUSTANG expression is still much higher than those observed in intact bone (FIG. 9B).

Figure 10:
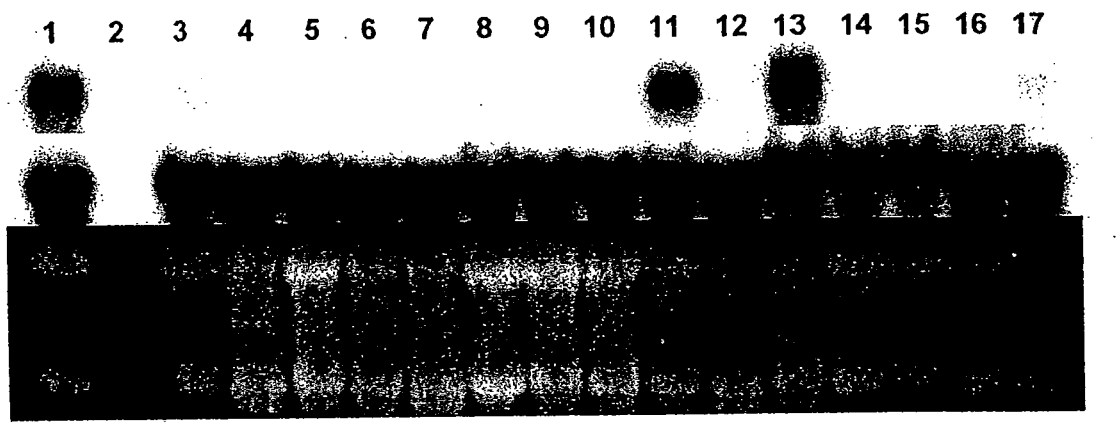
FIG. 10 shows adult tissue expression of mustang mRNA. Total RNA (15 ug) isolated from various adult tissue samples and analyzed via Northern blotting using randomly labeled probes. Lane 1, PF 5 callus RNA, lane 2, blank, and lanes 3–17 were loaded with intact bone (contains bone marrow, articular and normal growth plate cartilage), adrenal, brain, eye, heart, liver, lung, parotid, skeletal muscle, stomach, tendon, testis, thymus, thyroid and trachea, respectively. The RNA filter used in this analysis was initially hybridized with mustang (Top panel), stripped and then reprobed with an 18S rRNA probe (Middle Panel). The ethidium bromide stained RNA filter is also shown (Bottom Panel) to indicate the integrity and amounts of RNA loaded in each lane.

Next, we sought to determine weather MUSTANG was expressed in other adult tissues. Therefore, we extracted RNA from various organs, including intact bone, adrenal, brain, eye, heart, liver, lung, parotid, skeletal muscle, stomach, tendon, testis, thymus thyroid, and trachea and performed Northern blot analysis. Results from this experiment revealed robust expression only in skeletal muscle and tendon (FIG. 10). Skeletal muscle expression was expected since that was the tissue of origin for the mouse homologue (Accession #AJ277212). Lower levels of expression were detected in intact bone (consistent with results from FIG. 9) and trachea. In addition, other tissues (kidney, small intestine, and spleen) were screened for MUSTANG mRNA expression and again revealed no expression (data not shown), indicating that MUSTANG expression is exclusive to the musculoskeletal system.

EXAMPLE 9

Spatial Expression of MUSTANG mRNA. To reveal the cellular origin(s) of MUSTANG mRNA, in situ hybridization was utilized in conjunction with both sense and antisense riboprobes and sections derived from intact bone and PF day 5 and 14 fracture callus. Prior to hybridization, all tissue sections (intact, calluses and embryos) were thoroughly deparaffinized in xylene, washed and rehydrated in a graded series of EtOH washes. Protein digestion was then accomplished by incubation in 1N HCl, followed by another incubation with varying concentrations of Proteinase K (1 to 100 ug/ml, Roche). The sections were then acetylated with 0.5% acetic anhydride in PBS (pH 8.0), for 10 minutes with continuous stirring. Prior to hybridization, riboprobes in hybridization buffer were heated at 80° C. for 3 minutes, followed by quick cooling in ice water. The hybridization mixture, containing each riboprobe (1.0 ng/µl), 50% deionized formamide, 10% dextran sulfate, 2×SSC, 0.02% SDS, 0.01% salmon sperm DNA). The slides were incubated for 16 hr at 60° C. in a humid atmosphere. Following hybridization the sections were washed and the same anti-DIG detection assay was used. Finally, the sections were rinsed with tap water, mounted, and viewed with a Nikon microscope, and photographed using a digital camera (Sony DC330).

Figure 11:
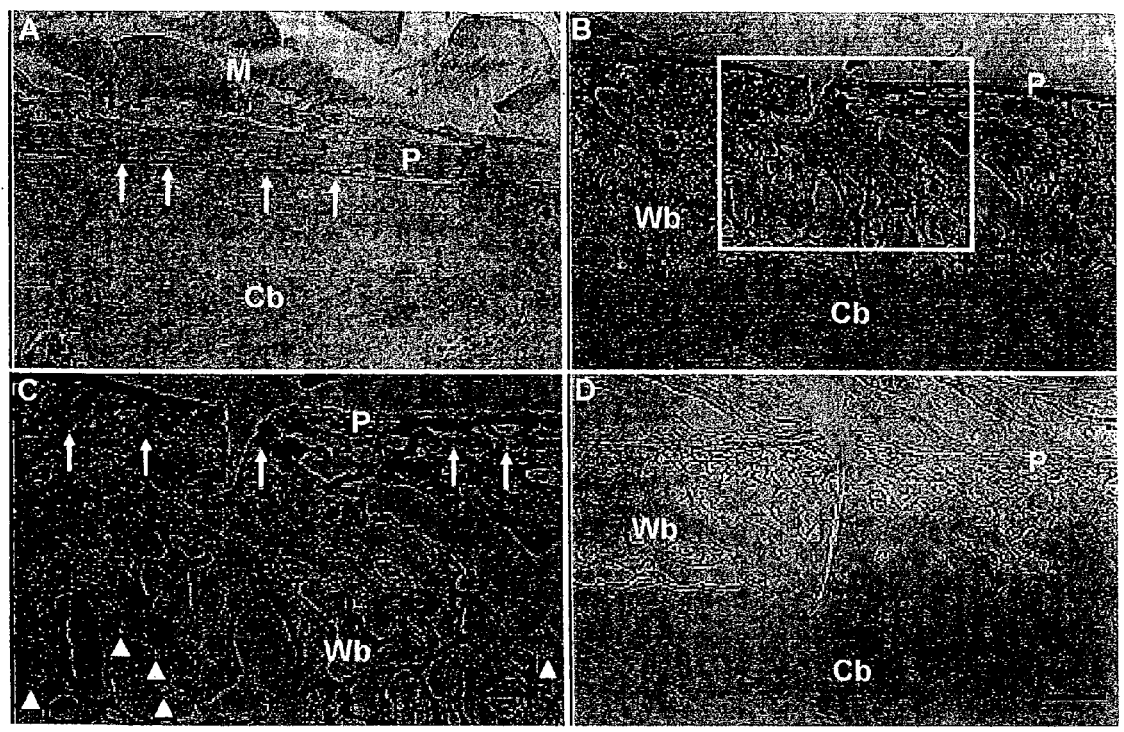
FIG. 11 shows in situ hybridization of mustang during early bone regeneration. Sections obtained from intact bone (A) and PF day 5 callus (B, C, D) were hybridized with a mustang antisense riboprobe. The area of the box in B is enlarged and shown in C. White arrows indicate mustang labeling in periosteal osteoprogenitors of intact bone (A), as well as young osteoblasts in a PF day 5 callus (B). Red arrowheads indicate the expression of mustang in trapped osteoblast (C) while red and white arrowheads show the gradual decrease and absence, respectively, of mustang expression in more mature osteoblasts/osteocytes (C). Cb, cortical bone, M, muscle, P, periosteum, Wb, woven bone. D shows an adjacent PF day 5 callus hybridized to a mustang sense riboprobe and indicates no expression. Scale bar in A and C=50 μm and in B and D=100 μm.

The PF day 5 callus was chosen because it corresponds to the highest levels of MUSTANG expression (see, FIG. 9), whereas the PF day 14 callus was selected because it represents a period of activity of cells involved in osteogenesis, chondrogenesis and endochondral ossification. (Jingushi S, Joyce M E, Bolander M E 1992 Genetic expression of extracellular matrix proteins correlates with histologic changes during fracture repair. J Bone Miner Res 7:1045–1055) MUSTANG expression in intact bone is localized in the osteogenic layer of the periosteum (FIG. 11A). Similarly, in a PF day 5 callus, MUSTANG is also expressed in the active periosteum but at much higher levels (FIGS. 11B, C). At higher magnification, it is clearly evident that these MUSTANG expressing osteogenic cells differentiate into mature osteoblasts that are responsible for the formation of woven bone (FIG. 11C, arrows). As these osteoblasts become trapped in the newly made osteoid (FIG. 11C, dark arrowheads) and further differentiate into mature osteocytes (FIG. 11C, white arrowheads), they cease expressing MUSTANG. FIG. 11D shows an adjacent section hybridized with the sense control MUSTANG riboprobe and demonstrates no labeling as expected.

Figure 12:
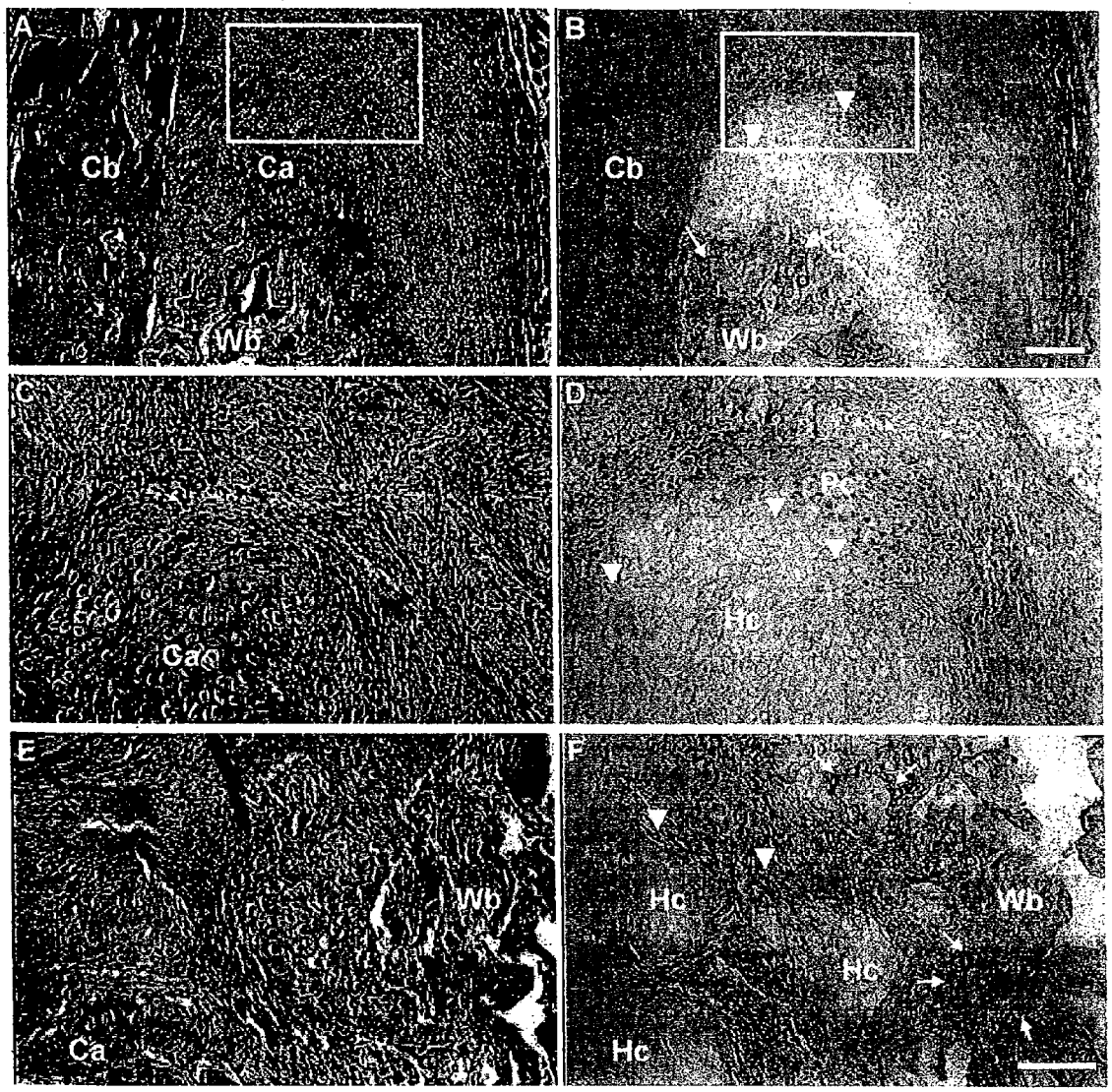
FIG. 12 shows in situ hybridization of mustang in a PF day 14 callus. Adjacent sections of a PF day 14 callus were either stained with safranin O-fast green (A, C, E) or hybridized to a mustang antisense riboprobe (B, D, E) and indicates the different tissues (cortical bone, Cb, cartilage, Ca, woven bone, Wb). The area within the boxes in A and B are enlarged and shown in C and D, respectively. Other specific regions are labeled as Hc, hypertrophic chondrocytes and Pc, proliferating chondrocytes. White arrowheads indicate mustang labeling in proliferating chondrocytes (B, D, F) whereas white arrows indicate young active osteoblasts in woven bone, wb, (B and F). Scale bar in A and B=200 μm and in C—F=100 μm.

Next, we investigated MUSTANG mRNA expression in a PF day 14 callus. In order to distinguish areas of cartilage from those of bone, sections were stained by safranin O-fast green (FIGS. 12A, C, E). The tissue sections were prepared following anesthesia. Postfractured femurs (days 3, 5, 7, 10, 14, and 21) and intact bones were carefully removed from each animal, cleared of soft tissue, fixed in 10% buffered formalin, decalcified in 5% formic acid, and embedded in paraffin (PolyFin, Polysciences, Inc). Serial longitudinal sections (10 mm) were cut from each bone and either stained with safranin O-fast green for the presence of cartilage (using standard histochemical procedures) or further processed for in situ hybridization. Rat embryo sections were purchased from Novagen and were prepared by fixation in 4% paraformaldehyde, embedded in paraffin and section at 7 mm thickness.

Adjacent sections were hybridized with the MUSTANG antisense riboprobe and revealed intense labeling in proliferating chondrocytes (FIG. 12B arrows, D arrowheads) and active osteoblasts (FIG. 12B, F arrows). Again, no signal was detected in the more mature and differentiated hypertrophic chondrocytes (FIG. 12D) or osteocytes within areas of intact bone (FIG. 7B) or newly made woven bone (FIG. 12F).

EXAMPLE 10

Figure 13:
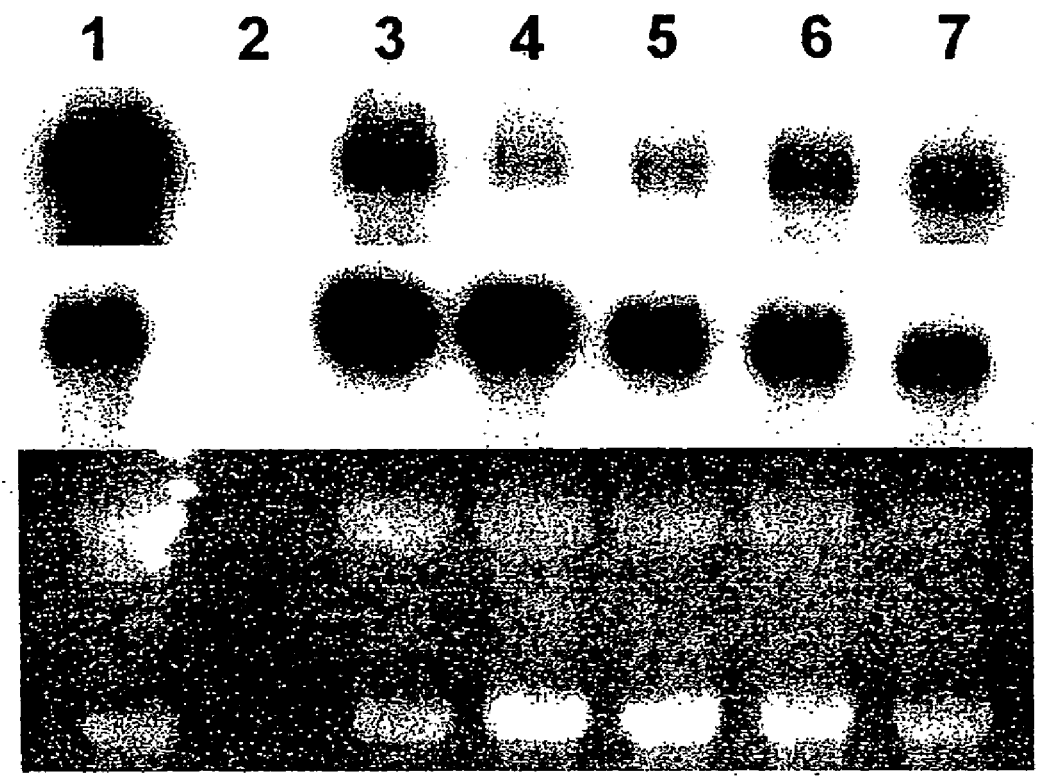
FIG. 13 shows embryonic expression of mustang mRNA. Total RNA from PF day 5 callus (lane 1) and whole embryos at E11, E14, E16, E18, and E20 (lanes 3, 4, 5, 6, 7, respectively) was analyzed by northern blotting using random labeled probes (mustang, Top panel and GAPDH, Middle panel). Lane 2 is empty. The RNA membrane used in this experiment is shown (Bottom panel) indicating the integrity and amounts of RNA loaded per lane.
Figure 14:
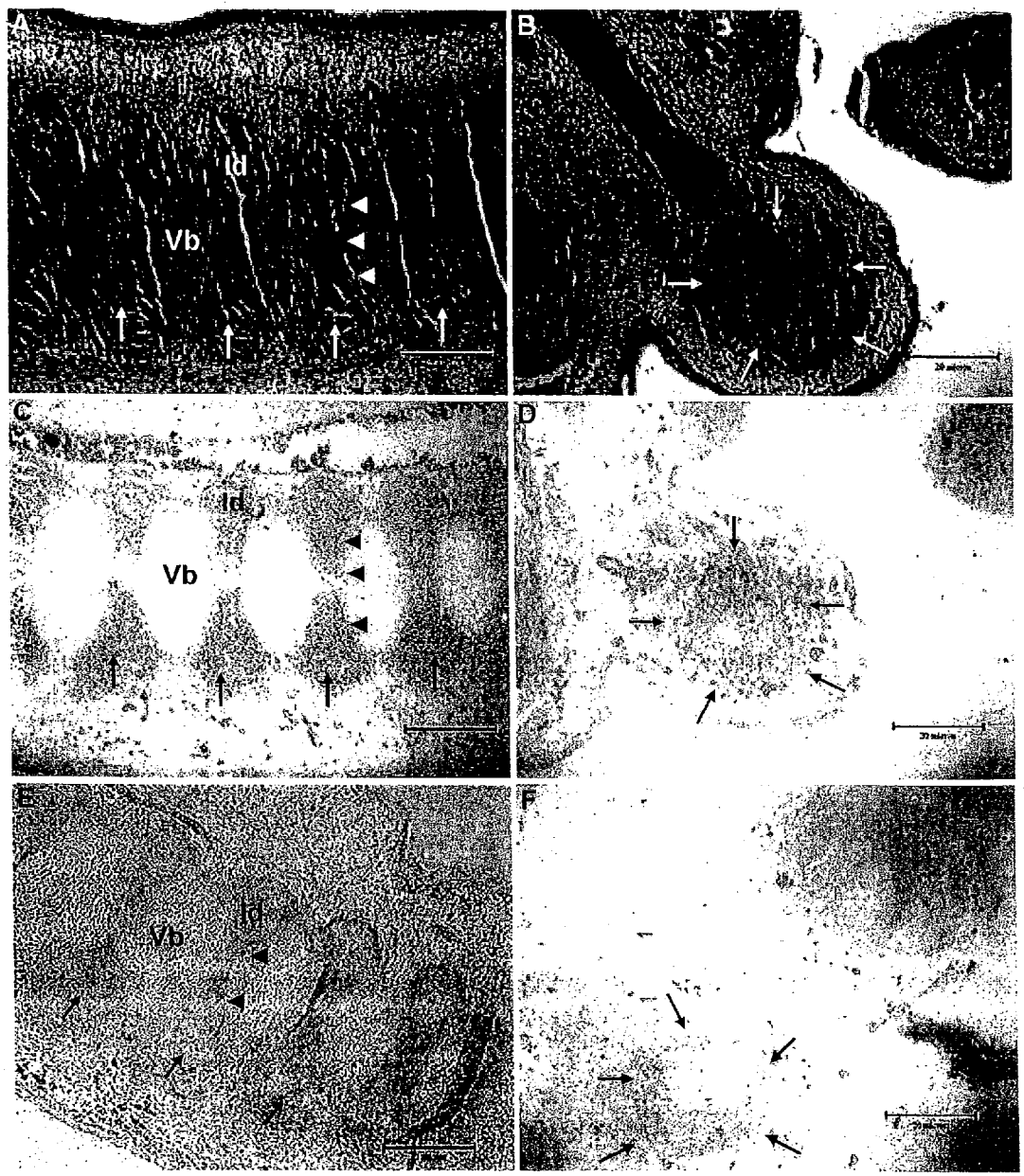
FIG. 14 shows in situ hybridization of MUSTANG during embryogenesis. Adjacent sections of a 16 day embryo (E16) were either stained with safranin O-fast green (A, B), hybridized to a mustang antisense riboprobe (C, D), or MUSTANG sense riboprobe (E, F). Arrowheads indicate mustang expression in perichondrium of developing vertebral bodies, Vb (C), whereas arrows indicate mesenchymal condensation in developing intervertebral discs (C) and digit (D). No expression was detected using the mustang sense riboprobe (E, F). For all photo micrographs, scale bar=20 μm.

Embryonic mRNA expression of MUSTANG. Since fracture repair is essentially a recapitulation of skeletal development, we decided to determine whether or not MUSTANG is expressed during embryonic bone development. Similar to our temporal and spatial expression studies with fracture calluses, rat embryos at different developmental stages (E11, E14, E16, E18, E20) were used as a source of total RNA. Northern analysis of these RNA samples revealed robust MUSTANG expression at all time points (FIG. 13, top panel). Since the RNA isolated from these samples was derived from whole embryos, we could not determine which particular tissue expresses MUSTANG. To address this question, we performed in situ hybridization on embryonic sections derived from E16, because at this stage the limb and tail buds are being formed and elongate. Abundant expression of MUSTANG was detected with the antisense riboprobe in the pericondrium of the tail vertebrae (FIG. 14C arrowheads) and mesenchymal cells of the intervertebral discs (FIG. 14C arrows). MUSTANG expression was also detected in mesenchymal cells of developing limbs (FIG. 14D arrows). As was the case with the callus, adjacent sections were stained with safranin O-fast green to clearly reveal cartilagenous areas (for comparison with hybridized sections, FIGS. 14A, B). Lastly, no expression was detected with the MUSTANG sense riboprobe (FIGS. 14E, F).

The riboprobes used above were prepared as follows: The 246 bp coding region of rat MUSTANG was subcloned into PCR TRAP vector (Gene Hunter). Orientation of sense and antisense strand was determined by DNA sequence analysis that revealed the position of the insert relative to the Sp6 and T7 promoters. The fragment was then PCR amplified using T7 and Sp6 Ribo Primers (Roche) and later purified (Roche PCR Clean-up Kit). The amplification and purification of both templates was confirmed by electrophoresis on a 1.5% agarose gel stained with ethidium bromide. In vitro transcription of the each cDNA was performed using DIG labeling kit (Roche) and was then digested by DNase. The RNA transcripts (both ribo probes) were again washed and purified using a PCR clean up protocol (supplied by the manufacturer). Their relative concentrations were determined by serial dot blot and DIG detection assay (Roche, DIG detection kit).

What is claimed is:

1. An isolated nucleic acid molecule comprising the nucleic acid sequence of SEQ ID NO: 1, that encodes a protein comprising the amino acid sequence of SEQ ID NO: 2, wherein said nucleic acid sequence is operably linked to a heterologous promoter.

2. A vector comprising the isolated nucleic acid of claim 1.

3. An isolated transformed host cell comprising the vector of claim 2.

4. The host cell of claim 3, wherein said host cell is selected from the group consisting of osteoblasts, osteocytes, osteoclasts, chondrocytes and cells of the peritoneal lining of the bone.

5. The host cell of claim 4, wherein said host cell was transfected with said vector under conditions wherein the protein encoded by SEQ ID NO: 1 is expressed.

6. A method for transfecting an isolated mammalian cell, comprising the steps of:
   a) providing:
      i) a target binding moiety capable of binding to a receptor selected from a group consisting of CD44 and osteopontin;
      ii) a nucleic acid binding moiety;
      iii) an expression vector comprising the nucleotide sequence set forth in SEQ ID NO:1; and
      iv) a maimmalian cell having on its exterior surface a receptor selected from the group consisting of CD44 receptor and osteopontin receptor;
   b) conjugating said target binding moiety to said nucleic acid binding moiety to form a carrier;
   c) coupling said expression vector with said carrier to form a pharmaceutical composition; and
   d) contacting said mammalian cell with said pharmaceutical composition under conditions such that said mammalian cell is transfected.

7. The method of claim 6, wherein said mammalian cell is selected from the group consisting of osteoblasts, osteocytes, osteoclasts, chondrocytes and cells of the peritoneal lining of the bone.

* * * * *

SEQUENCE LISTING

<160> NUMBER OF SEQ ID NOS: 7

<210> SEQ ID NO 1
<211> LENGTH: 1025
<212> TYPE: DNA
<213> ORGANISM: Rattus norvegicus
<220> FEATURE:
<221> NAME/KEY: CDS
<222> LOCATION: (262)..(507)

<400> SEQUENCE: 1

```
gagcagctgt cccgagatac gggatacccc ctgtccatct gctctcccca gggtggctgc      60
ccatcatgtc caagaataaa ctccagctag tccctgcgtg gatctgaatc atctgagagc     120
ttccaaagga ggggagtgac tacccaggac gcacaggcag gctatataag ttcccaaggg     180
ctgggctcca cacagatctt tgcctgtggc tactgcctgc tgccagagag ttaccaaaag     240
agagcttgct tggcatctac c atg tcc gag gct ggc act cct gaa gcc ccc       291
                        Met Ser Glu Ala Gly Thr Pro Glu Ala Pro
                          1               5                  10 atc aag aag aag cgc ccc cct gtg aag gaa gaa gac ctg aag ggg gcc       339
Ile Lys Lys Lys Arg Pro Pro Val Lys Glu Glu Asp Leu Lys Gly Ala
                 15                  20                  25 cgg ggg agt ctg tcc aag aac cag gag atc aag tct aag acg tac cag       387
Arg Gly Ser Leu Ser Lys Asn Gln Glu Ile Lys Ser Lys Thr Tyr Gln
             30                  35                  40 gtc atg cgg gac tat gag caa gct ggc tca gct gcc cca tct ata ttc       435
Val Met Arg Asp Tyr Glu Gln Ala Gly Ser Ala Ala Pro Ser Ile Phe
         45                  50                  55 agc cgc aac cgc acg ggc acc gag aca gtc ttc gag aag ccc aaa gag       483
Ser Arg Asn Arg Thr Gly Thr Glu Thr Val Phe Glu Lys Pro Lys Glu
     60                  65                  70 gga cct gcc aag agc gtc ttt ggc tgagaagtgc actttgcact acaccctgg      537
Gly Pro Ala Lys Ser Val Phe Gly
 75                  80 gcacagcaac ctgtccacga actctctctc tctctctttt ttttttttta atgctggaag     597
atgcttttcc tctgccacct ctggaaccat cttgactgtc acaaccctag cccttggaaa     657
caccaataaa gaatacgcca cttgggaagg taccatggcc actacctgca gaagagaggg     717
acagcatatt gagtgcccctt cctggtcccc gaggtgggtc ggggaatgat gtgtgtgctt    777
tcagaaccac tgaggtgttc tagaaagagc cttagacatg gagtcctgat acggactttc     837
tgacggatgt agacttgtct gttttctcta aatctctgtt ttaggctgga aagacggtgc     897
catagctaag agtacttgct gtttctttag aggacgctgg ttcaattccc aaacagccgc     957
atggctgctc ataaccattt aactctgcca ccctcttctg gcctctgcgg gcattgcata    1017
cacgtggt                                                             1025
```

<210> SEQ ID NO 2
<211> LENGTH: 82
<212> TYPE: PRT
<213> ORGANISM: Rattus norvegicus

<400> SEQUENCE: 2

Met Ser Glu Ala Gly Thr Pro Glu Ala Pro Ile Lys Lys Lys Arg Pro
1               5                   10                  15

Pro Val Lys Glu Glu Asp Leu Lys Gly Ala Arg Gly Ser Leu Ser Lys
                20                  25                  30

Asn Gln Glu Ile Lys Ser Lys Thr Tyr Gln Val Met Arg Asp Tyr Glu
            35                  40                  45

Gln Ala Gly Ser Ala Ala Pro Ser Ile Phe Ser Arg Asn Arg Thr Gly
        50                  55                  60

Thr Glu Thr Val Phe Glu Lys Pro Lys Glu Gly Pro Ala Lys Ser Val
65                  70                  75                  80

Phe Gly

<210> SEQ ID NO 3
<211> LENGTH: 9
<212> TYPE: PRT
<213> ORGANISM: Rattus norvegicus

<400> SEQUENCE: 3

Pro Ile Lys Lys Lys Arg Pro Pro Val
1               5

<210> SEQ ID NO 4
<211> LENGTH: 6
<212> TYPE: DNA
<213> ORGANISM: Rattus norvegicus

<400> SEQUENCE: 4 aataaa                                                                6

<210> SEQ ID NO 5
<211> LENGTH: 82
<212> TYPE: PRT
<213> ORGANISM: Mus musculus

<400> SEQUENCE: 5

Met Ser Glu Ala Gly Thr Pro Glu Gly Pro Ile Lys Lys Lys Arg Pro
1               5                   10                  15

Pro Val Lys Glu Glu Asp Leu Lys Gly Ala Arg Gly Thr Leu Ala Lys
                20                  25                  30

Asn Gln Asp Ile Lys Ser Lys Thr Tyr Gln Val Met Arg Asp Tyr Glu
            35                  40                  45

Gln Ala Gly Ser Ala Ala Pro Ser Val Phe Ser Arg Asn Arg Thr Gly
        50                  55                  60

Thr Glu Thr Val Phe Glu Lys Pro Lys Glu Gly Pro Ala Lys Ser Val
65                  70                  75                  80

Phe Gly

<210> SEQ ID NO 6
<211> LENGTH: 82
<212> TYPE: PRT
<213> ORGANISM: Homo sapiens

<400> SEQUENCE: 6

```
Met Ser Gln Ala Gly Ala Gln Glu Ala Pro Ile Lys Lys Lys Arg Pro
1               5                   10                  15

Pro Val Lys Glu Glu Asp Leu Lys Gly Ala Arg Gly Asn Leu Thr Lys
                20                  25                  30

Asn Gln Glu Ile Lys Ser Lys Thr Tyr Gln Val Met Arg Glu Cys Glu
            35                  40                  45

Gln Ala Gly Ser Ala Ala Pro Ser Val Phe Ser Arg Thr Arg Thr Gly
        50                  55                  60

Thr Glu Thr Val Phe Glu Lys Pro Lys Ala Gly Pro Thr Lys Ser Val
65                  70                  75                  80

Phe Gly

<210> SEQ ID NO 7
<211> LENGTH: 82
<212> TYPE: PRT
<213> ORGANISM: Bos taurus

<400> SEQUENCE: 7

Met Ser Gln Ala Gly Ala Gln Glu Ala Pro Ile Lys Lys Lys Arg Pro
1               5                   10                  15

Pro Val Lys Glu Glu Asp Leu Lys Gly Ala Arg Gly Asn Leu Thr Lys
                20                  25                  30

Asn Gln Glu Ile Lys Ser Lys Thr Tyr Gln Val Met Arg Glu Cys Glu
            35                  40                  45

Gln Ala Gly Ser Thr Ala Pro Ser Val Phe Ser Arg Ala Arg Thr Gly
        50                  55                  60

Ala Glu Thr Val Phe Glu Lys Pro Lys Ala Gly Pro Ala Lys Ser Val
65                  70                  75                  80

Phe Gly
```